(12) United States Patent
Taylor et al.

(10) Patent No.: US 8,637,038 B2
(45) Date of Patent: Jan. 28, 2014

(54) METHODS FOR INHIBITING ALLOGRAFT REJECTION

(75) Inventors: Vanessa Taylor, San Francisco, CA (US); Esteban Masuda, Menlo Park, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 13/444,684

(22) Filed: Apr. 11, 2012

(65) Prior Publication Data
US 2012/0263737 A1    Oct. 18, 2012

Related U.S. Application Data

(60) Provisional application No. 61/474,606, filed on Apr. 12, 2011.

(51) Int. Cl.
*A61K 39/00* (2006.01)
*A01N 43/54* (2006.01)
*A01N 43/00* (2006.01)

(52) U.S. Cl.
USPC .................... 424/184.1; 514/210.21; 514/275

(58) Field of Classification Search
None
See application file for complete search history.

(56) References Cited

U.S. PATENT DOCUMENTS

| | | | |
|---|---|---|---|
| 7,947,698 | B2 | 5/2011 | Atuegbu et al. |
| 2007/0203161 | A1 | 8/2007 | Argade et al. |
| 2008/0260754 | A1 | 10/2008 | Li et al. |
| 2010/0190770 | A1* | 7/2010 | Li et al. .................... 514/210.21 |
| 2010/0331359 | A1 | 12/2010 | Menet et al. |

FOREIGN PATENT DOCUMENTS

WO    WO 2010/020905    2/2010

OTHER PUBLICATIONS

Deuse et al. Novel Immunosuppression:R348, a JAK3-and Syk-inhibitor attenuates acute cardiac allograft rejection. Transplantation. 85(6). Mar. 27, 2008.*
Ayrout et al. Experimental limb transplantation, part 1: identification of an effective tapered triple combination immunosuppressive regime. Transplantation Proceedings. 36: 669-674, 2004.*
Behbod et al., "Concomitant Inhibition of Janus Kinase 3 and Calcineurin-Dependent Signaling Pathways Synergistically Prolongs the Survival of Rat Heart Allografts," *The Journal of Immunology*, vol. 166, pp. 3724-3732, 2001.
Deuse et al., Novel Immunosuppression: R348, a JAK3- and Syk-Inhibitor Attenuates Acute Cardiac Allograft Rejection, *Transplantation*, vol. 85, pp. 885-892, 2008.

* cited by examiner

*Primary Examiner* — Vanessa L Ford
*Assistant Examiner* — Sandra Dillahunt
(74) *Attorney, Agent, or Firm* — Klarquist Sparkman, LLP

(57) ABSTRACT

Disclosed herein are methods for treating or inhibiting allograft rejection in a transplant recipient. In some embodiments, the methods include administering to the transplant recipient a first amount of a JAK1/3 inhibitor comprising 5-(2-(4-fluoro-3-methoxy-5-methylphenylamino)-5-methylpyrimidin-4-ylamino)benzo[d]oxazol-2(3H)-one (Compound I) or a prodrug thereof and administering to the transplant recipient a second amount of a non-JAK1/3 inhibitor immunosuppressant, wherein the combined effect of the first amount and the second amount is greater than the effect of the first amount or the second amount individually, wherein the JAK1/3 inhibitor acts in combination with the non-JAK1/3 inhibitor immunosuppressant to inhibit or treat allograft rejection. In some embodiments at least one of the first amount or the second amount is individually a suboptimal dose for inhibiting or treating allograft rejection. In some examples, the combined effect of the first amount and the second amount to inhibit or treat allograft rejection in the transplant recipient is synergistic.

24 Claims, 9 Drawing Sheets

METHODS FOR INHIBITING ALLOGRAFT REJECTION

CROSS REFERENCE TO RELATED APPLICATION

This claims the benefit of U.S. Provisional Application No. 61/474,606, filed Apr. 12, 2011, which is incorporated herein by reference in its entirety.

FIELD

This disclosure relates to methods for treating or inhibiting allograft rejection in a transplant recipient, particularly utilizing combination therapy with a JAK1/3 inhibitor and a non-JAK1/3 inhibitor immunosuppressant.

BACKGROUND

Immunosuppressive therapy after organ transplantation is essential for treatment or prevention of allograft rejection and long-term survival of grafts. Currently used immunosuppressants, such as calcineurin inhibitors, mTOR inhibitors, and purine or pyrimidine inhibitors generally provide adequate immunosuppression, but also cause a broad spectrum of unwanted systemic side effects (such as infection, organ toxicity, and metabolic disturbances) and drug-drug interactions.

Calcineurin inhibitors such as cyclosporine and tacrolimus (Tac) are widely used in immunosuppressive therapy in transplant recipients. For example, 94% of kidney transplant recipients receive a calcineurin inhibitor immunosuppressant immediately following transplantation (Naesens et al., *Clin. J. Am. Soc. Nephrol.* 4:481-508, 2009). However, the side effects of these drugs, particularly nephrotoxicity, cause substantial morbidity and ultimately limit long-term graft and patient survival.

SUMMARY

Approaches to reducing immunosuppressant side effects (such as calcineurin inhibitor-associated nephrotoxicity) include short-term use of the immunosuppressant following allograft transplantation, or longer-term, lower dose therapies. However, these approaches can result in increased risk of rejection for transplant recipients (Naesens et al., *Clin. J. Am. Soc. Nephrol.* 4:481-509, 2009). It is has surprisingly been found by the inventors that low or suboptimal dose therapy with a traditional immunosuppressant in combination with a JAK1/3 inhibitor results in allograft survival to a greater extent than either of the compounds administered individually, and in some cases with a synergistic effect. Thus, effectively treating, inhibiting, or even preventing allograft rejection in a transplant recipient may be accomplished while reducing immunosuppressant-associated side effects.

Disclosed herein are methods for inhibiting or treating allograft rejection in a transplant recipient. In some embodiments, the methods include administering to the transplant recipient a first amount of a Janus kinase (JAK) 1/3 inhibitor including 5-(2-(4-fluoro-3-methoxy-5-methylphenylamino)-5-methylpyrimidin-4-ylamino)benzo[d]oxazol-2(3H)-one (Compound I) or a prodrug thereof and administering to the transplant recipient a second amount of a non-JAK1/3 inhibitor immunosuppressant, wherein the combined effect of the first amount and the second amount is greater than the effect of the first amount or the second amount individually, wherein the JAK1/3 inhibitor acts in combination with the non-JAK1/3 inhibitor immunosuppressant to inhibit or treat allograft rejection. In other embodiments, the methods include administering to the transplant recipient a first amount of a JAK 1/3 inhibitor including Compound I or a prodrug thereof and administering to the transplant recipient a second amount of a non-JAK1/3 inhibitor immunosuppressant, wherein at least one of the first amount or the second amount is individually a suboptimal dose for inhibiting or treating allograft rejection, and wherein the combined effect of the first amount and the second amount is greater than the effect of the first amount or the second amount individually, wherein the JAK1/3 inhibitor acts in combination with the non-JAK1/3 inhibitor immunosuppressant to inhibit or treat allograft rejection. In some examples, the combined effect of the first amount and the second amount to inhibit or treat allograft rejection in the transplant recipient is synergistic.

In some embodiments, the non-JAK1/3 inhibitor immunosuppressant includes a calcineurin inhibitor, an inhibitor of mTOR, an inhibitor of inosine monophosphate dehydrogenase (IMPDH), an anti-T-cell antibody, or a combination of two or more thereof. In some examples, the non-JAK1/3 inhibitor immunosuppressant is a calcineurin inhibitor, such as tacrolimus, cyclosporine, or pimecrolimus. In a particular example, the calcineurin inhibitor is tacrolimus.

In further embodiments, the JAK1/3 inhibitor includes a prodrug of Compound I, such as sodium-(5-(2-(4-fluoro-3-methoxy-5-methylphenylamino)-5-methylpyrimidin-4-ylamino)-2-oxobenzo[d]oxazol-3(2H)-yl)methyl phosphate (Compound II).

The disclosed methods include administering the recited compounds (or one or more pharmaceutical compositions including the compounds) to a transplant recipient, for example, a subject who has received a heart transplant, a lung transplant, a liver transplant, or a kidney transplant. The methods include inhibiting or treating hyperacute allograft rejection, acute allograft rejection, chronic allograft rejection, or a combination of two or more thereof.

The foregoing and other features of the disclosure will become more apparent from the following detailed description, which proceeds with reference to the accompanying figures.

DETAILED DESCRIPTION

I. Abbreviations

Figure 1:
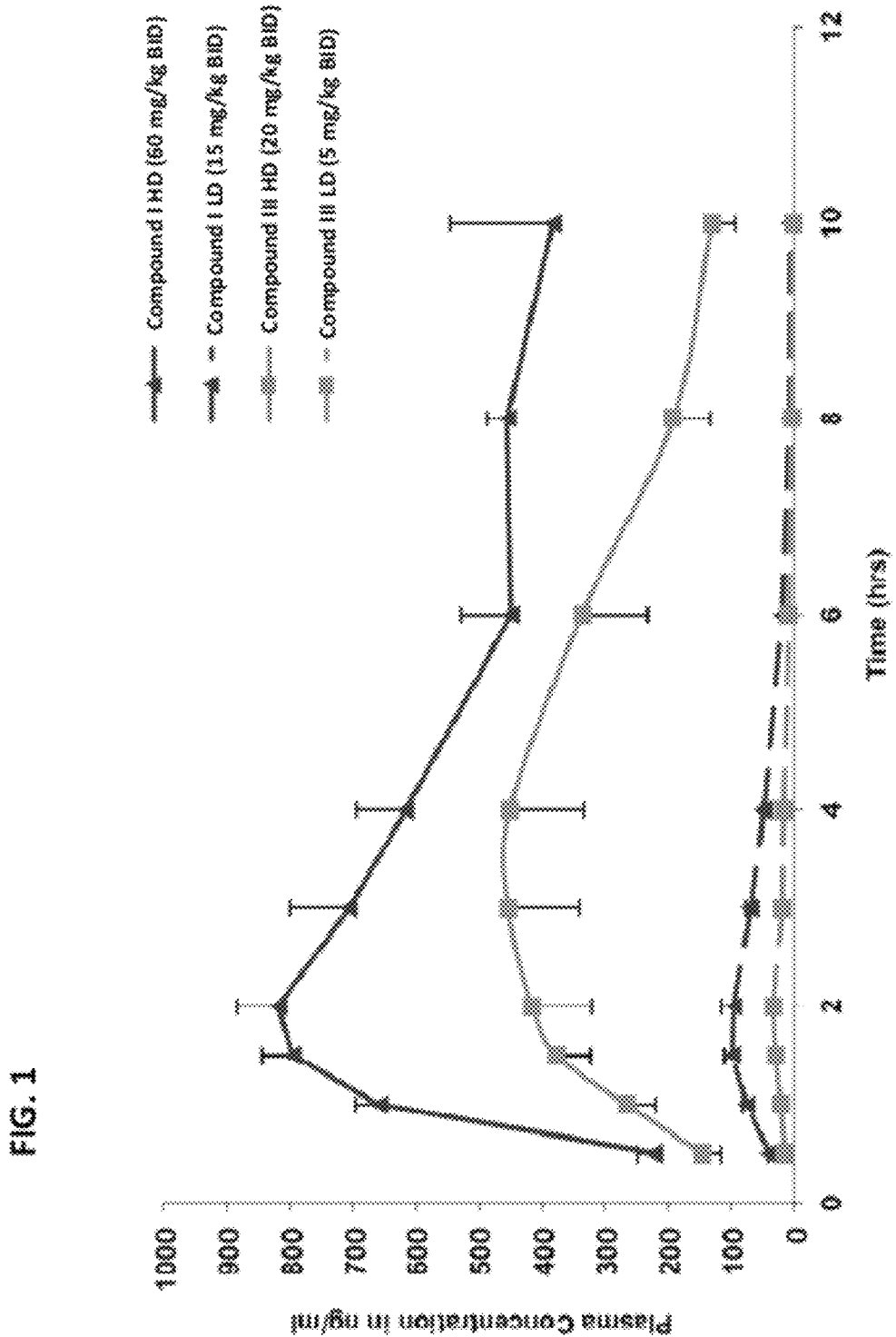
FIG. 1 is a graph showing plasma concentration of 5-(2-(4-fluoro-3-methoxy-5-methylphenylamino)-5-methylpyrimidin-4-ylamino)benzo[d]oxazol-2(3H)-one (Compound I) or 5-(2-(3-methoxy-4,5-dimethylphenylamino)-5-methylpyrimidin-4-ylamino)benzol[d]oxazol-2-(3H)-one (Compound III) followed for 10 hours in male Lewis rats dosed at the indicated concentrations. HD, high dose; LD, low dose.

AUC area under the curve
BN Brown Norway rats
CHEP cultured human erythroid progenitor cells
CI combination index
Compound I 5-(2-(4-fluoro-3-methoxy-5-methylphenylamino)-5-methylpyrimidin-4-ylamino)benzo[d]oxazol-2(3H)-one
Compound II sodium-(5-(2-(4-fluoro-3-methoxy-5-methylphenylamino)-5-methylpyrimidin-4-ylamino)-2-oxobenzo[d]oxazol-3(2H)-yl)methyl phosphate
Compound III 5-(2-(3-methoxy-4,5-dimethylphenylamino)-5-methylpyrimidin-4-ylamino)benzol[d]oxazol-2-(3H)-one
DSA donor-specific antibodies
EPO erythropoietin
HD high dose
H+E hematoxylin and eosin
IFN interferon
IL interleukin
IMPDH inosine monophosphate dehydrogenase
JAK Janus kinase
LD low dose
Lew Lewis rats
MCP-1 monocyte chemotactic protein-1
MLR mixed lymphocyte reaction
mTOR mammalian target of rapamycin
Tac tacrolimus
Th T helper cell

II. Terms

Unless otherwise noted, technical terms are used according to conventional usage. Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Although methods and materials similar or equivalent to those described herein can be used in the practice or testing of the present disclosure, suitable methods and materials are described below.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

5-(2-(4-fluoro-3-methoxy-5-methylphenylamino)-5-methylpyrimidin-4-ylamino)benzo[d]oxazol-2(3H)-one (Compound I)

A compound having the structure:

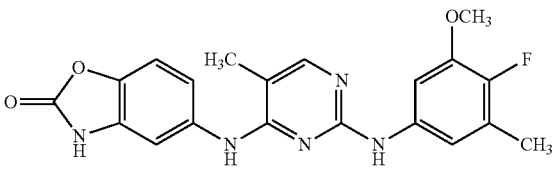 [SMILES: COc1cc(Nc2ncc(C)c(Nc3ccc4oc(=O)[nH]c4c3)n2)cc(C)c1F]

Compound I is JAK1/3 kinase inhibitor (see, e.g., International Patent Publication No. WO 2010/085684, incorporated herein by reference).

5-(2-(3-methoxy-4,5-dimethylphenylamino)-5-methylpyrimidin-4-ylamino)benzol[d]oxazol-2-(3H)-one (Compound III): A compound having the structure:

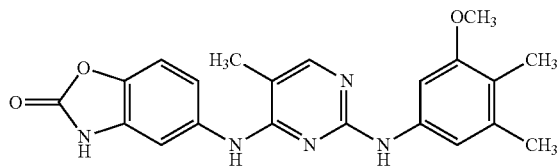 [SMILES: COc1cc(Nc2ncc(C)c(Nc3ccc4oc(=O)[nH]c4c3)n2)cc(C)c1C]

Compound III is a JAK1/3 kinase inhibitor (see, e.g., International Patent Publication No. WO 2010/085684, incorporated herein by reference).

Sodium-(5-(2-(4-fluoro-3-methoxy-5-methylphenylamino)-5-methylpyrimidin-4-ylamino)-2-oxobenzo[d]oxazol-3(2H)-yl)methyl phosphate (Compound II)

A compound having the structure:

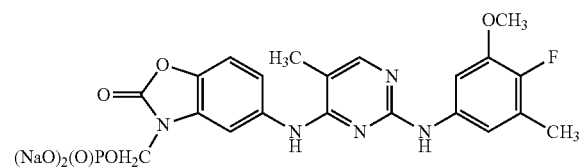

Compound II is a prodrug of the JAK1/3 kinase inhibitor Compound I (see,. e.g., International Patent Publication No. WO 2010/085684, incorporated herein by reference).

Administering: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Allograft rejection: An "allograft" is a transplant of an organ, tissue, bodily fluid or cell from one individual to a genetically non-identical individual of the same species. "Allograft rejection" as used herein refers to a partial or complete immune response to a transplanted cell, tissue, organ, or the like on or in a recipient of said transplant due to an immune response to an allograft. Allografts can be rejected through either a cell-mediated or humoral immune reaction of the recipient against histocompatability antigens present on the donor cells. The strongest antigens include the human leukocyte group A (HLA) antigens.

Calcineurin inhibitor: A class of immunosuppressant compounds that inhibit the phosphatase activity of calcineurin. Calcineurin inhibitors act for example, by binding to an immunophilin (such as cyclophilin or FKBP1A) followed by binding of the complex to calcineurin and inhibition of the phosphatase activity of calcineurin. Exemplary calcineurin inhibitors include cyclosporine, tacrolimus, pimecrolimus, and voclosporin.

Immunosuppressant: Any compound that decreases the function or activity of one or more aspects of the immune system, such as a component of the humoral or cellular immune system or the complement system. Immunosuppressants are also referred to as "immunosuppressive agents."

In some examples, an immunosuppressant is a "non-JAK1/3 inhibitor immunosuppressant," which includes immunosuppressant compounds that do not inhibit (for example, do not substantially inhibit) activity of JAK1 and/or JAK3. Such non-JAK1/3 inhibitor immunosuppressants include, but are not limited to: (1) antimetabolites, such as purine synthesis inhibitors (such as inosine monophosphate dehydrogenase (IMPDH) inhibitors, e.g., azathioprine, mycophenolate, and mycophenolate mofetil), pyrimidine synthesis inhibitors (e.g., leflunomide and teriflunomide), and antifolates (e.g., methotrexate); (2) calcineurin inhibitors, such as tacrolimus, cyclosporine A, pimecrolimus, and voclosporin; (3) TNF-α inhibitors, such as thalidomide and lenalidomide; (4) IL-1 receptor antagonists, such as anakinra; (5) mammalian target of rapamycin (mTOR) inhibitors, such as rapamycin (sirolimus), deforolimus, everolimus, temsirolimus, zotarolimus, and biolimus A9; (6) corticosteroids, such as prednisone; and (7) antibodies to any one of a number of cellular or serum targets (including anti-lymphocyte globulin and anti-thymocyte globulin).

Exemplary cellular targets and their respective inhibitor compounds include, but are not limited to complement component 5 (e.g., eculizumab); tumor necrosis factors (TNFs) (e.g., infliximab, adalimumab, certolizumab pegol, afelimomab and golimumab); IL-5 (e.g., mepolizumab); IgE (e.g., omalizumab); BAYX (e.g., nerelimomab); interferon (e.g., faralimomab); IL-6 (e.g., elsilimomab); IL-12 and IL-13 (e.g., lebrikizumab and ustekinumab); CD3 (e.g., muromonab-CD3, otelixizumab, teplizumab, visilizumab); CD4 (e.g., clenoliximab, keliximab and zanolimumab); CD11a (e.g., efalizumab); CD18 (e.g., erlizumab); CD20 (e.g., afutuzumab, ocrelizumab, pascolizumab); CD23 (e.g., lumiliximab); CD40 (e.g., teneliximab, toralizumab); CD62L/L-selectin (e.g., aselizumab); CD80 (e.g., galiximab); CD147/basigin (e.g., gavilimomab); CD154 (e.g., ruplizumab); BLyS (e.g., belimumab); CTLA-4 (e.g., ipilimumab, tremelimumab); CAT (e.g., bertilimumab, lerdelimumab, metelimumab); integrin (e.g., natalizumab); IL-6 receptor (e.g., tocilizumab); LFA-1 (e.g., odulimomab); and IL-2 receptor/CD25 (e.g., basiliximab, daclizumab, inolimomab).

Inhibiting or treating a condition: "Inhibiting" a condition or disease refers to inhibiting the full development of a condition or disease, for example allograft rejection in a subject. In contrast, "treatment" refers to a therapeutic intervention that ameliorates a sign or symptom of a condition or disease after it has begun to develop. A subject to be administered with an amount of the pharmaceutical composition to inhibit or treat the disease or condition can be identified by standard diagnosing techniques for such a disorder, for example, basis of family history, or risk factor to develop the disease or disorder.

JAK1/3 inhibitor: Janus kinases (JAK) are a family of cytoplasmic protein tyrosine kinases including JAK1, JAK2, JAK3, and TYK2. Upon binding of cytokines to the receptors (such as IL-2, IL-4, IL-7, IL-9, IL-15, and IL-21), cytoplasmic tails of associated JAKs are brought into proximity and trans-phosphorylation of tyrosine residues of the JAKs occurs, resulting in JAK activation. In some examples, 2,4-pyrimidinediamine compounds (such as those described in International Publication No. WO 2010/085684, incorporated herein by reference) are inhibitors of JAKs. In some examples, a JAK1/3 inhibitor is a compound that selectively inhibits JAK1 and/or JAK3 activity, for example, inhibits JAK1 and JAK3 activity to a greater extent than it inhibits JAK2 and/or TYK2 activity. In a particular example, a JAK1/3 inhibitor is 54244-fluoro-3-methoxy-5-methylphenylamino)-5-methylpyrimidin-4-ylamino)benzo[d]oxazol-2 (3H)-one (Compound I).

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of the agents disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A salt of a compound, which salts are derived from a variety of organic and inorganic counterions, for example, sodium, potassium, calcium, magnesium, ammonium, or tetraalkylammonium, or when the molecule contains a basic functionality, salts of organic or inorganic acids, such as hydrochloride, hydrobromide, tartrate, mesylate, acetate, maleate, or oxalate. Pharmaceutically acceptable acid addition salts are salts that retain the biological effectiveness of the free bases while formed by acid partners that are not biologically or otherwise undesirable, for example, inorganic acids (such as hydrochloric acid, hydrobromic acid, sulfuric acid, nitric acid, or phosphoric acid) or organic acids (such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, or salicylic acid). Pharmaceutically acceptable base addition salts include those derived from inorganic bases such as sodium, potassium, lithium, ammonium, calcium, magnesium, iron, zinc, copper, manganese, or aluminum salts. Exemplary salts are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethylaminoethanol, 2-diethylaminethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethypiperidine, polyamine resins, and the like. Exemplary organic bases are isopropylamine, diethylamine, ethanolamine, trimethylamine, dicyclohexylamine, choline, and caffeine. See, e.g., *Handbook of Pharmaceutical Salts, Properties, Selection and Use*, Wiley VCH (2002); Berge et al., *J. Pharm. Sci.* 66:1-19, 1977.

Prodrug: A compound that is transformed in vivo to yield the parent compound, for example by hydrolysis in the gut or enzymatic conversion in blood. Common examples include, but are not limited to ester and amide forms of a compound having an active form bearing a carboxylic acid moiety. See, e.g., *Prodrugs as Novel Delivery Systems*, Eds., Higuchi and Stella, ACS Symposium Series, Vol. 14, 1975; *Bioreversible Carriers in Drug Design*, ed. Roche, Pergamon Press, 1987.

Subject: Living multi-cellular vertebrate organisms, a category that includes both human and non-human mammals. In some examples, a subject is a transplant recipient (for example a subject that has received an organ transplant, such as a liver, heart, lung, or kidney transplant).

Suboptimal dose: An amount of an agent that does not result in a therapeutic effect (such as treating or inhibiting allograft rejection in a transplant recipient) or that produces a less than optimal therapeutic effect. In some examples, it is desirable to administer a suboptimal dose of a therapeutic agent to a subject, for example to decrease the occurrence or severity of side effects (for example, nephrotoxicity in the case of calcineurin inhibitor immunosuppressants). One of skill in the art can determine a suboptimal dose, taking into account the subject, type and severity of condition being treated, therapeutic agent, and so on.

In some specific examples of the disclosed methods, the agent is tacrolimus and a suboptimal dose includes a dose of less than about 0.2 mg/kg, such as a dose of less than about 0.15, 0.1, 0.09, 0.08, 0.07, 0.06, 0.05, 0.04, 0.03, 0.02 mg/kg, or less in a human subject.

Synergistic effect: The action of two or more agents (such as two or more therapeutics) producing an effect greater than the total effect of each agent individually, for example, a greater than an additive effect. Methods for determining whether two or more agents produce a synergistic effect are known to one of skill in the art. In some examples, synergism is determined using an isobologram (see, e.g., Tallarida, *J. Pharmcol. Exp. Ther.* 298:865-872, 2001). A point "below the line" on the isobologram indicates synergism, while a point "above the line" on the isobologram indicates a subadditive or antagonistic effect. In other examples, a synergistic effect of two or more compounds is determined using the combination index (CI). See, e.g., Chou, in *Synergism and Antagonism in Chemotherapy*, Chou and Rideout, eds, pp. 61-102, Academic Press, 1991; Chou, Pharmacol. Rev. 68:621-681, 2006. A CI value of <1 indicates synergism; a CI value equal to 1 indicates an additive effect; and a CI value >1 indicates antagonism. Dose-effect curves and CI values can be determined utilizing commercially available software, such as CalcuSyn (Biosoft, Cambridge, United Kingdom) or CompuSyn (ComboSyn Inc., Paramus, N.J.).

Tacrolimus: Also known as FK506 or fujimycin, a calcineurin inhibitor immunosuppressant drug. Tacrolimus is a 23-membered macrolide lactone first discovered in the fermentation broth of a Japanese soil sample that contained the bacteria *Streptomyces tsukubaensis*. This compound is often used after allogeneic organ transplant to reduce the activity of the patient's immune system and lower the risk of allograft rejection. Tacrolimus reduces T-cell and interleukin-2 activity. It is also used in a topical preparation in the treatment of severe atopic dermatitis (eczema), severe refractory uveitis after bone marrow transplants, and the skin condition vitiligo.

Therapeutically effective amount: An amount of a compound or a combination of compounds sufficient to treat or inhibit a disease or condition, such as allograft rejection in a transplant recipient. The amount of a compound or combination of compounds which is a therapeutically effective amount will vary depending on the compound, the disease or condition and its severity, the age of the subject, and so on. A therapeutically effective amount can be determined by one of skill in the art.

III. Methods of Treating or Inhibiting Allograft Rejection

Disclosed herein are methods of treating or inhibiting (or in some instances, even preventing) allograft rejection in a transplant recipient. The methods include administering a combination of a JAK1/3 inhibitor and a non-JAK1/3 inhibitor immunosuppressant to the transplant recipient. In some examples, the amount of the JAK1/3 inhibitor and/or the non-JAK1/3 inhibitor immunosuppressant administered to the transplant recipient is a reduced amount (for example, less than standard dosing) or a suboptimal amount and is effective for inhibiting or treating allograft rejection, but with a potentially reduced number, severity, and/or duration of side effects.

In some embodiments, the methods include administering to the transplant recipient a first amount of a JAK 1/3 inhibitor including 5-(2-(4-fluoro-3-methoxy-5-methylphenylamino)-5-methylpyrimidin-4-ylamino)benzo[d]oxazol-2 (3H)-one (Compound I) or a prodrug thereof, and administering to the transplant recipient a second amount of a non-JAK1/3 inhibitor immunosuppressant, wherein the combined effect of the first amount and the second amount is greater than the effect of the first amount or the second amount individually, wherein the JAK1/3 inhibitor acts in combination with the non-JAK1/3 inhibitor immunosuppressant to inhibit or treat allograft rejection.

In other embodiments, the methods include administering to the transplant recipient a first amount of a JAK 1/3 inhibitor including Compound I or a prodrug thereof, and administering to the transplant recipient a second amount of a non-JAK1/3 inhibitor immunosuppressant, wherein at least one (or both) of the first amount or the second amount is individually a suboptimal dose for inhibiting or treating allograft rejection, and wherein the combined effect of the first amount and the second amount is greater than the effect of the first amount or the second amount individually, wherein the JAK1/3 inhibitor acts in combination with the non-JAK1/3 inhibitor immunosuppressant to inhibit or treat allograft rejection. A suboptimal dose (for example, a suboptimal dose of Compound I or a non-JAK1/3 inhibitor immunosuppressant, such as a calcineurin inhibitor) includes an amount that does not result in a therapeutic effect (such as treating or inhibiting allograft rejection in a transplant recipient) or produces a less than optimal therapeutic effect. In some examples, it is desirable to administer a suboptimal dose of at least one therapeutic agent to a subject, for example to decrease the occurrence or severity of side effects (for example, nephrotoxicity in the case of calcineurin inhibitor immunosuppressants).

In some examples, the combined effect of the first amount (e.g., the amount of Compound I or a prodrug thereof) and the second amount (e.g., the amount of a non-JAK1/3 inhibitor immunosuppressant, such as a calcineurin inhibitor) to inhibit or treat allograft rejection in a transplant recipient is greater than the individual effect of either the first amount or second amount. In some examples, the combined effect of the first amount and the second amount to inhibit or treat allograft rejection in a transplant recipient is additive or substantially additive. In other examples, the combined effect of the first amount and the second amount to inhibit or treat allograft rejection in a transplant recipient is synergistic.

One of skill in the art can determine whether the combined effect of the JAK1/3 inhibitor Compound I or a prodrug thereof and the non-JAK1/3 inhibitor immunosuppressant (such as a calcineurin inhibitor, for example, tacrolimus) is greater than the effect of either compound individually to treat or inhibit allograft rejection in a transplant recipient. Methods for evaluating drug combination effects (such as additivity or synergism) include isobolar analysis or the additive composite curve (Tallarida, *J. Pharmacol. Exp. Ther.* 298:865-872, 2001), the Bliss independence model (Bliss, *Ann. Appl. Biol.* 26:585-615, 1939), the Loewe additivity model (Loewe, *Arzneim-Forsch* 3:285-290, 1953), the Chou-Talalay Combination Index (CI; Chou and Talalay, *Trends Pharmacol. Sci.* 4:450-454, 1983; Chou and Talalay, *Adv. Enzyme Regul.* 22:27-55, 1984; Chou, *Cancer Res.* 70:440-446, 2010), and others (e.g., Yan et al., *BMC Systems Biol.* 4:50, 2010). In particular examples, a combination of a JAK1/3 inhibitor (such as Compound I) and a non-JAK1/3 inhibitor immunosuppressant (such as tacrolimus) has a greater effect for treating or inhibiting allograft rejection than either compound individually if their CI is less than or equal to 1. In some examples, a CI of 1 indicates that the combined effect of Compound I and the non-JAK1/3 inhibitor immunosuppressant is additive. In other examples, a CI of less than 1 indicates that the combined effect of Compound I and the non-JAK1/3 inhibitor immunosuppressant is synergistic. In particular embodiments, as a result of the combined effect of Compound I (or a prodrug thereof) and the non-JAK1/3 inhibitor immunosuppressant, one or both of the agents can be administered to the transplant recipient at a dose that is less than the amount if the agent is administered individually, resulting in decreased side effects (such as organ toxicity).

In particular embodiments, the methods disclosed herein include administering a JAK1/3 inhibitor such as Compound I or prodrug thereof (for example, Compound II) to a transplant recipient to treat or inhibit allograft rejection. Compound I is a 2,4-pyrimidinediamine compound having the structure:

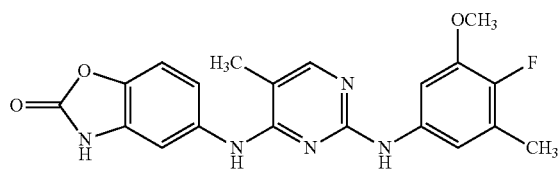 [SMILES: COc1cc(Nc2ncc(C)c(Nc3ccc4oc(=O)[nH]c4c3)n2)cc(C)c1F]

Compound II is a prodrug form of Compound I having the structure:

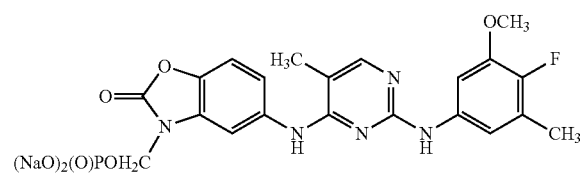

These compounds, methods of their synthesis, and methods for assessing inhibition of JAK kinases (such as JAK1 and JAK3) are described in International Patent Publication No. WO 2010/085684, incorporated herein by reference.

The methods disclosed herein also include administering a non-JAK1/3 inhibitor immunosuppressant to a transplant recipient to treat, inhibit, or even prevent allograft recipient. A non-JAK1/3 inhibitor immunosuppressant includes an immunosuppressant compound that does not substantially inhibit JAK1 or JAK3 kinase activity. In some examples, the non-JAK1/3 inhibitor immunosuppressant inhibits a JAK1 or JAK3 kinase pathway (such as T-cell proliferation in response to IL-2, CD23 upregulation in B cells in response to IL-4, or upregulation of ICAM-1 in response to IFN-γ in A549 or U937 cells) with an $IC_{50}$ of about 100 μM or more (such as 200 μM, 500 μM, 1 mM, or more). One of skill in the art can determine whether a particular immunosuppressant inhibits JAK1/3 kinase activity using routine methods.

In some embodiments, a non-JAK1/3 inhibitor immunosuppressant is a calcineurin inhibitor immunosuppressant. Examples, of calcineurin inhibitor immunosuppressants include cyclosporin (e.g., SANDIMMUNE®, CICLORAL®, or GENGRAF®), tacrolimus (e.g., PROGRAF®), pimecrolimus, and voclosporin. In a particular embodiment of the disclosed methods, the non-JAK1/3 inhibitor immunosuppressant is tacrolimus.

In other embodiments, a non-JAK1/3 inhibitor immunosuppressant includes an inhibitor of mTOR, such as sirolimus (rapamycin, RAPAMUNE®), everolimus (ZORTRESS®), temsirolimus, deforolimus, zotarolimus, or biolimus A9; an IMPDH inhibitor, e.g., azathioprine (AZASAN®), mycophenolate (MYFORTIC®), or mycophenolate mofetil (CELLCEPT®); a TNF-α inhibitor, such as thalidomide (THALOMID®) or lenalidomide (REVLIMID®); an IL-1 receptor antagonist, such as anakinra (KINERET®); or an antibody to any one of a number of cellular or serum targets (such as those listed above).

In some embodiments, the transplant recipient is a subject who has received an organ or other tissue transplant, such as one or more of a liver transplant, a kidney transplant, a heart transplant, a lung transplant, a bone marrow transplant, a small bowel transplant, a pancreas transplant, a trachea transplant, a skin transplant, a cornea transplant, or a limb transplant. In specific examples, the transplant recipient has received a heart transplant, a lung transplant, a liver transplant, or a kidney transplant. In some embodiments, the disclosed methods include administering the JAK 1/3 inhibitor to a tissue or organ prior to transplanting the tissue or organ in the transplant recipient.

The disclosed methods are useful for treating or inhibiting (or even preventing) allograft rejection in a transplant recipient. The methods may treat or inhibit any type of allograft rejection, including hyperacute rejection, acute rejection, and/or chronic rejection. Hyperacute rejection occurs within hours to days following transplantation and is mediated by a complement response in recipients with pre-existing antibodies to the donor. In hyperacute rejection, antibodies are observed in the transplant vasculature very soon after transplantation, leading to clotting, ischemia, and eventual necrosis and death. Hyperacute rejection is relatively rare due to pre-transplant screening (for example, for ABO blood type antibodies). Acute rejection occurs days to months following transplantation. It is a T-cell mediated response and is identified based on presence of T-cell infiltration of the transplanted tissue, structural injury to the transplanted tissue, and injury to the vasculature of the transplanted tissue. Finally, chronic rejection occurs months to years following transplantation and is associated with chronic inflammatory and immune response against the transplanted tissue. Chronic rejection may also include chronic allograft vasculopathy, which is associated with fibrosis of vasculature of the transplanted tissue. One of skill in the art can diagnose allograft rejection type and severity in a transplant recipient.

IV. Pharmaceutical Compositions and Administration

Pharmaceutical compositions that include a JAK1/3 inhibitor, such as

Compound I or a prodrug thereof (such as Compound II) can be formulated with an appropriate pharmaceutically acceptable carrier, depending upon the particular mode of administration chosen. Likewise, a non-JAK1/3 inhibitor immunosuppressant, such as a calcineurin inhibitor, can be formulated with an appropriate pharmaceutically acceptable carrier, depending upon the particular mode of administration chosen. Compositions that includes a JAK1/3 inhibitor, such as Compound I or a prodrug thereof (such as Compound II) and a non-JAK1/3 inhibitor immunosuppressant, such as a calcineurin inhibitor (for example, tacrolimus), can also be formulated with an appropriate pharmaceutically acceptable carrier, depending upon the particular mode of administration chosen.

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually comprise injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate.

In some embodiments, the JAK1/3 inhibitor Compound I or prodrug thereof (such as Compound II) is included in a controlled release formulation, for example, a microencapsulated formulation. In other embodiments, the non-JAK1/3 inhibitor immunosuppressant is included in a controlled release formulation, for example, a microencapsulated formulation. Various types of biodegradable and biocompatible polymers can be used, and methods of encapsulating a variety of synthetic compounds, proteins and nucleic acids, have been well described in the art (see, for example, U.S. Pat. Publication Nos. 2007/0148074; 2007/0092575; and 2006/0246139; U.S. Pat. Nos. 4,522,811; 5,753,234; and 7,081,489; PCT Publication No. WO/2006/052285; Benita, *Microencapsulation: Methods and Industrial Applications*, 2$^{nd}$ ed., CRC Press, 2006).

In other embodiments, the JAK1/3 inhibitor Compound I or prodrug thereof (such as Compound II) is included in a nanodispersion system. In further embodiments, the non-JAK1/3 inhibitor immunosuppressant is included in a nanodispersion system. Nanodispersion systems and methods for producing such nanodispersions are well known to one of skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), and poly (ethylene glycol). Exemplary low molecular weight surfactants include sodium dodecyl sulfate, hexadecyl pyridinium chloride, polysorbates, sorbitans, poly(oxyethylene) alkyl ethers, poly(oxyethylene) alkyl esters, and combinations thereof. In some examples, the nanodispersion is prepared using the solvent evaporation method. See, e.g., Kanaze et al., *Drug Dev. Indus. Pharm.* 36:292-301, 2010; Kanaze et al., *J. Appl. Polymer Sci.* 102:460-471, 2006.

In some examples, Compound I or a prodrug thereof (such as Compound II), includes a pharmaceutically acceptable salt of such compounds. Suitable pharmaceutically acceptable salts are derived from a variety of organic and inorganic counterions, for example, sodium, potassium, calcium, magnesium, ammonium, or tetraalkylammonium, or when the molecule contains a basic functionality, salts of organic or inorganic acids, such as hydrochloride, hydrobromide, tartrate, mesylate, acetate, maleate, or oxalate. By way of example, Compound I may be administered as the free base or as a pharmaceutically acceptable acid addition salt. Pharmaceutically acceptable acid addition salts are salts that retain the biological effectiveness of the free bases while formed by acid partners that are not biologically or otherwise undesirable, for example, inorganic acids (such as hydrochloric acid, hydrobromic acid, sulfuric acid, nitric acid, or phosphoric acid) or organic acids (such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, benzene sulfonic acid, ethanesulfonic acid, p-toluenesulfonic acid, 1-hydroxy-2-napthoic acid or salicylic acid). By way of example, Compound II may be administered as the corresponding free acid, or a pharmaceutically acceptable base addition salt such as the illustrated disodium salt salt or another pharmaceutically acceptable base addition salt. Pharmaceutically acceptable base addition salts include those derived from inorganic bases such as alkali metal bases, alkaline earth metal bases, or other metal bases to give counterions including sodium, potassium, lithium, ammonium, calcium, magnesium, iron, zinc, copper, manganese, or aluminum salts. As understood by those of skill in the art, different addition salts may be formed with the same counterion, for example, the mono or disodium salt of Compound II may be formed. Exemplary salts are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines, and basic ion exchange resins, such as isopropylamine, trimethylamine, diethylamine, triethylamine, tripropylamine, ethanolamine, 2-dimethylaminoethanol, 2-diethylaminethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethypiperidine, polyamine resins, and the like. Exemplary organic bases are isopropylamine, diethylamine, ethanolamine, trimethylamine, dicyclohexylamine, choline, and caffeine. These salts may be prepared by standard procedures, for example by reacting the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Description of suitable pharmaceutically acceptable salts can be found in *Handbook of Pharmaceutical Salts, Properties, Selection and Use*, Wiley VCH (2002); Berge et al., *J. Pharm. Sci.* 66:1-19, 1977.

The dosage form of the pharmaceutical compositions will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The compounds of this disclosure can be administered to humans or other animals on whose tissues they are effective in various manners such as orally, intravenously, intramuscularly, intraperitoneally, intranasally, intradermally, intrathecally, subcutaneously, via inhalation or via suppository. In one non-limiting example, the compound is administered orally. In another non-limiting example, the compound is administered intravenously. The particular mode of administration and the dosage regimen will be selected by the attending clinician, taking into account the particulars of the case (e.g. the subject, the disease, the disease state involved, and whether the treatment is prophylactic). Treatment can involve daily or multi-daily doses of compound(s) over a period of a few days to months, or even years. In a particular example, treatment involves a twice daily doses of Compound I or a prodrug thereof and a single daily dose of a non-JAK1/3 inhibitor immunosuppressant, such as a calcineurin inhibitor (for example, cyclosporin or tacrolimus).

Site-specific administration of the disclosed compounds can be used, for instance by administering Compound I (or a prodrug thereof) or a non-JAK1/3 inhibitor immunosuppressant (such as a calcineurin inhibitor, for example tacrolimus) to the lungs or respiratory tract to treat or inhibit allograft rejection in a transplant recipient (for example, a lung transplant recipient). By way of example, one method of administration to the lungs of an individual is by inhalation through the use of a nebulizer or inhaler. For example, the compound (such as Compound I or a calcineurin inhibitor) is formulated in an aerosol or particulate and drawn into the lungs using a standard nebulizer well known to those skilled in the art. Other routes of administration to the lungs or respiratory tract include bronchial, intranasal, or other inhalatory routes. In some examples the compound is administered by inhalation (for example, by inhaling an aerosol); direct installation in the lung via a bronchoscope, endotracheal tube, or an artificial ventilation device; nasal administration (intranasal or transnasal); bronchial, or intratracheally (for example, by injection directly into the trachea or tracheostomy).

One of skill in the art can identify appropriate doses for the JAK1/3 inhibitor (such as Compound I or a prodrug thereof) and the non-JAK1/3 inhibitor immunosuppressants (such as a calcineurin inhibitor) of use in the disclosed methods. The amount administered will be dependent on factors such as the subject being treated, the type and severity of the condition (for example, the type of allograft and type of rejection (such as hyperacute, acute, or chronic rejection)), and the mode of administration. The non-JAK1/3 inhibitor immunosuppressants may be used according to standard or common dosages, for example as in commercially available forms or as described in the 2006 edition of *The Physician's Desk Reference* (Thomspon PDR, Montvale, N.J.). In some examples of the disclosed methods, the amount of the non-JAK1/3 inhibitor immunosuppressant administered to the subject may be less than the standard dose (such as a suboptimal dose).

A pharmaceutical composition that includes the JAK1/3 inhibitor Compound I or a prodrug thereof (such as Compound II) can be formulated in unit dosage form, suitable for individual administration of precise dosages. In one specific, non-limiting example, a unit dosage contains from about 1 mg to about 5 g of Compound I or its equivalent in the form of a prodrug thereof (such as about 100 mg to about 2.5 g, about 250 mg to about 1 g, or about 500 mg to about 750 mg). In some examples, a unit dosage contains about 1 mg, 10 mg, 25 mg, 50 mg, 75 mg, 100 mg, 150 mg, 200 mg, 250 mg, 500 mg, 750 mg, 1 g, 1.5 g, 2 g, 2.5 g, 3 g, 4 g, or 5 g of Compound I or a prodrug thereof. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

In some examples, a therapeutically effective amount of Compound I or a prodrug thereof (when administered in combination with a non-JAK1/3 inhibitor immunosuppressant) is about 0.5 mg/kg to about 100 mg/kg (for example, about 1 mg/kg to about 50 mg/kg, about 10 mg/kg to about 25 mg/kg, or about 1 mg/kg to about 15 mg/kg). In a specific example, a therapeutically effective amount of Compound I or a prodrug thereof (when administered in combination with a non-JAK1/3 inhibitor immunosuppressant) is from about 0.5 mg/kg to about 7 mg/kg or from about 1 mg/kg to about 12 mg/kg or from about 10 mg/kg to about 20 mg/kg, such as about 15 mg/kg. In some examples, a therapeutically effective amount of Compound I or a prodrug thereof (when administered in combination with a non-JAK1/3 inhibitor immunosuppressant) is about 0.5 mg/kg/day to about 100 mg/kg/day (for example, about 1 mg/kg/day to about 60 mg/kg/day, about 10 mg/kg/day to about 30 mg/kg/day, or about 1 mg/kg/day to about 30 mg/kg/day). In additional examples, a therapeutically effective amount of Compound I or a prodrug thereof (when administered in combination with a non-JAK1/3 inhibitor immunosuppressant) is about 0.5 mg/kg/day, 1 mg/kg/day, 2.5 mg/kg/day, 5 mg/kg/day, 7.5 mg/kg/day, 10 mg/kg/day, 15 mg/kg/day, 20 mg/kg/day, 25 mg/kg/day, 50 mg/kg/day, 75 mg/kg/day, or 100 mg/kg/day. One of skill in the art can extrapolate from an animal dose (such as a rat or mouse) to an appropriate human dose (see, e.g., Reagan-Shaw et al., *FASEB J.* 22:659-661, 2008).

A therapeutically effective amount of Compound I or a prodrug thereof administered in combination with a non-JAK1/3 inhibitor immunosuppressant can be the amount of Compound I or a prodrug thereof necessary to treat or inhibit allograft rejection in a transplant recipient. A therapeutically effective amount of Compound I or a prodrug thereof administered in combination with a non-JAK1/3 inhibitor immunosuppressant can be administered in a single dose, or in several doses, for example weekly, bi-weekly, daily, or twice daily, during a course of treatment. One of skill in the art can determine the therapeutically effective amount of Compound I or a prodrug thereof administered in combination with a non-JAK1/3 inhibitor immunosuppressant based for example, on the subject being treated, the severity and type of the affliction, and the manner of administration of the therapeutic(s).

A pharmaceutical composition that includes a non-JAK1/3 inhibitor immunosuppressant (for example, a calcineurin inhibitor, an IMPDH inhibitor, or mTOR inhibitor) can be formulated in unit dosage form, suitable for individual administration of precise dosages. In one specific, non-limiting example, a unit dosage contains from about 0.1 mg to about 5 g of a non-JAK1/3 inhibitor immunosuppressant (such as about 0.5 mg to about 2.5 g, about 1 mg to about 1 g, about 1 mg to about 1 g, or about 100 mg to about 5 g). In some examples, a unit dosage contains about 0.1 mg, 0.2 mg, 0.5 mg, 1 mg, 5 mg, 10 mg, 25 mg, 50 mg, 75 mg, 100 mg, 250 mg, 500 mg, 750 mg, 1 g, 1.5 g, 2 g, 2.5 g, 3 g, 4 g, or 5 g of a non-JAK1/3 inhibitor immunosuppressant. The amount of active compound(s) administered will be dependent on the particular non-JAK1/3 inhibitor immunosuppressant, the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

In some examples, a therapeutically effective amount of the non-JAK1/3 inhibitor immunosuppressant (for example, a calcineurin inhibitor, an IMPDH inhibitor, or mTOR inhibitor) administered in combination with a JAK1/3 inhibitor such as Compound I or a prodrug thereof is about 0.01 mg/kg to about 50 mg/kg (for example, about 0.1 mg/kg to about 40 mg/kg, about 1 mg/kg to about 25 mg/kg, or about 1 mg/kg to about 15 mg/kg). In a specific example, a therapeutically effective amount of tacrolimus administered in combination with Compound I or a prodrug thereof is about 1 mg/kg to about 5 mg/kg, such as about 1 mg/kg. In some examples, a therapeutically effective amount of a non-JAK1/3 inhibitor immunosuppressant (when administered in combination with Compound I or a prodrug thereof) is about 0.01 mg/kg/day to about 50 mg/kg/day (for example, about 0.5 mg/kg/day to about 25 mg/kg/day, about 1 mg/kg/day to about 10 mg/kg/day, or about 1 mg/kg/day to about 5 mg/kg/day). In additional examples, a therapeutically effective amount of a non-JAK1/3 inhibitor immunosuppressant (when administered in combination with Compound I or a prodrug thereof) is about 0.01 mg/kg/day, 0.02 mg/kg/day, 0.05 mg/kg/day, 0.1 mg/kg/day, 0.25 mg/kg/day, 0.5 mg/kg/day, 0.75 mg/kg/day, 1 mg/kg/day, 2 mg/kg/day, 3 mg/kg/day, 4 mg/kg/day, 5 mg/kg/day, 7.5 mg/kg/day, 10 mg/kg/day, 15 mg/kg/day, or 20 mg/kg/day.

In some specific examples of the disclosed methods, the non-JAK1/3 inhibitor is tacrolimus. One of skill in the art can select the dose of tacrolimus administered to the transplant recipient. In some examples, the methods include administering tacrolimus to the transplant recipient at a dose of about 0.01-0.2 mg/kg/day. In a particular example, the method includes administering a suboptimal dose to of tacrolimus to the transplant recipient such as a dose of less than about 0.2 mg/kg, such as a dose of less than about 0.15, 0.1 0.09, 0.08, 0.07, 0.06, 0.05, 0.04, 0.03, 0.02 mg/kg in a human subject. One of skill in the art can extrapolate from an animal dose (such as a rat or mouse) to an appropriate human dose (see, e.g., Reagan-Shaw et al., *FASEB J.* 22:659-661, 2008). Other factors include the subject being treated, the severity of the affliction, and the manner of administration, which can be taken into account by one of skill in the art in selecting an appropriate dose of tacrolimus.

A therapeutically effective amount of a non-JAK1/3 inhibitor immunosuppressant (for example, a calcineurin inhibitor, an IMPDH inhibitor, or mTOR inhibitor) can be the amount of a non-JAK1/3 inhibitor immunosuppressant administered in combination with Compound I or a prodrug thereof necessary to treat or inhibit allograft rejection in a transplant recipient. A therapeutically effective amount of a non-JAK1/3 inhibitor immunosuppressant can be administered in a single dose, or in several doses, for example weekly, biweekly, daily, or twice daily, during a course of treatment. One of skill in the art can determine the therapeutically effective amount of a non-JAK1/3 inhibitor immunosuppressant administered in combination with Compound I or a prodrug thereof based for example, on the subject being treated, the severity and type of the affliction, and the manner of administration of the therapeutic(s).

A pharmaceutical composition that includes the JAK1/3 inhibitor Compound I or a prodrug thereof (such as Compound II) and a non-JAK1/3 inhibitor immunosuppressant (such as a calcineurin inhibitor, for example, tacrolimus) can be formulated in unit dosage form, suitable for individual administration of precise dosages. In one specific, non-limiting example, such a composition includes from about 1 mg to about 5 g of Compound I or a prodrug thereof (such as about 100 mg to about 2.5 g, about 250 mg to about 1 g, or about 500 mg to about 750 mg) and from about 0.1 mg to about 5 g of a non-JAK1/3 inhibitor immunosuppressant (such as about 0.5 mg to about 2.5 g, about 1 mg to about 1 g, about 1 mg to about 1 g, or about 100 mg to about 5 g). In one non-limiting example, the composition includes Compound I and tacrolimus. In another non-limiting example, the composition includes Compound II and tacrolimus. A therapeutically effective amount of the composition including Compound I or a prodrug thereof and a non-JAK1/3 inhibitor immunosuppressant can be administered in a single dose, or in several doses, for example weekly, bi-weekly, daily, or twice daily, during a course of treatment. One of skill in the art can determine the therapeutically effective amount of a non-JAK1/3 inhibitor immunosuppressant and Compound I or a prodrug thereof based for example, on the subject being treated, the severity and type of the affliction, and the manner of administration of the therapeutic(s).

In some examples, the methods disclosed herein include gradually reducing (tapering) the dose of the non-JAK1/3 inhibitor immunosuppressant administered to the transplant recipient in combination with the Compound I or a prodrug thereof. In one example, the dose of the non-JAK1/3 inhibitor immunosuppressant is tapered until only the JAK1/3 inhibitor Compound I or a prodrug thereof is administered to the transplant recipient. Tapering of non-JAK1/3 inhibitor immunosuppressant drugs (such as calcineurin inhibitors or mTOR inhibitors) is well known to one of skill in the art. In some examples, the non-JAK1/3 inhibitor immunosuppressant is administered as a series of tapered doses, for example, a linear taper of about 5-25%. For example, the dosage of the non-JAK1/3 inhibitor immunosuppressant is reduced by about 5-25% (such as about 5%, 10%, 15%, 20%, or 25%) per unit time (such as per day, per week, or per month). In a particular example, the non-JAK1/3 inhibitor immunosuppressant is tacrolimus and the tacrolimus is administered as a series of tapered doses. One of skill in the art can select an appropriate series of tapered doses based on the particular non-JAK1/3 inhibitor immunosuppressant, the subject being treated, the severity and type of affliction, and the manner of administration of the therapeutic(s).

When the JAK1/3 inhibitor Compound I (or a prodrug thereof) and a non-JAK1/3 inhibitor immunosuppressant (such as a calcineurin inhibitor, for example tacrolimus) are administered to a transplant recipient, the administration can be sequential, simultaneous (concurrent), or substantially simultaneous. Sequential administration can be separated by any amount of time, so long as the desired affect is achieved. Multiple administrations of the compositions described herein are also contemplated. The combined administration of the JAK1/3 inhibitor compound I or a prodrug thereof and a non-JAK1/3 inhibitor immunosuppressant includes administering the non-JAK1/3 inhibitor immunosuppressant either sequentially with the JAK1/3 inhibitor Compound I (or a prodrug thereof), e.g., the treatment with one agent first and then the second agent, or administering both agents at substantially the same time, e.g., an overlap in performing the administration. With sequential administration a subject is exposed to the agents at different times so long as some amount of the first agent remains in the subject (or has a therapeutic effect) when the other agent is administered. The treatment with both agents at the same time can be in the same dose, e.g., physically mixed, or in separate doses administered at the same time.

A subject having allograft rejection (for example, acute or chronic allograft rejection) or at risk of allograft rejection (such as a subject that has received an allograft) is a candidate for treatment using the therapeutic methods disclosed herein.

The following examples are provided to illustrate certain particular features and/or embodiments. These examples should not be construed to limit the disclosure to the particular features or embodiments described.

EXAMPLES

Example 1

Materials and Methods

In Vivo Pharmacokinetics:

Male Lewis rats were orally administered at dosages of Compound I HD (60 mg/kg/BID); Compound I LD (15 mg/kg/BID); Compound III HD (20 mg/kg/BID), and Compound III LD (5 mg/kg/BID), respectively. Plasma levels of drugs were quantified 0.5, 1, 1.5, 2, 3, 4, 6, 8, and 10 hours after administration. Plasma levels of Compound I and Compound III were quantified by LC/MS/MS.

Pharmacodynamics:

The activity of Compound III and Compound I was assessed in a panel of cell-based assays. Compound III and Compound I are selective inhibitors of JAK1/3-dependent signaling. Data for a non-selective JAK inhibitor (Compound IV) is shown for reference. Mixed lymphocyte reactions (MLRs) were performed by incubating freshly prepared naive human peripheral blood lymphocytes from one donor with CD80+/CD86+ mature Dendritic Cells derived from a different donor for 5 days. The percentage of CD3+/CD71+ (anti-CD3-APC, Clone HIT3a, anti-CD 71-FITC, Clone M-A712; BD Biosciences, San Jose, Calif.) proliferating cells was assessed by fluorescence-activated cell sorting (FACS; BD Bioscience). Interleukin-2 (IL-2)-dependent human primary T cell proliferation was assessed using CellTiter-Glo® Luminescent Cell Viability Assay (Promega, Madison, Wis.). STAT phosphorylation induced by different cytokines in human primary T cells was measured by intracellular FACS analysis (anti-pY694-STAT5 AlexaFluor488, anti-pY701-STAT1 AlexaFluor488, and anti-pY693-STAT4 AlexaFluor488; BD Biosciences). STAT phosphorylation induced by different cytokines was performed in whole blood after red blood cell lysis (Lyse/Fix buffer, BD Biosciences) and methanol permeabilization. Interferon-γ (IFN-γ) signaling was assessed in the U937 monocytic cell line by measuring ICAM-1 surface expression by FACS (ICAM-1-APC, BD Bioscience).

The erythropoietin (EPO)-dependent survival of cultured human erythroid progenitor cells (CHEPs) was determined using CellTiter-Glo® Luminescent Cell Viability Assay (Promega). Human primary T cell activation was assessed by measuring IL-2 production by ELISA (R&D Systems, Minneapolis, Minn., USA) following plate-bound anti-CD3 and anti-CD28 stimulation (Anti-Human CD3; BD Biosciences; Anti-Human CD28; Immunotech; Prague, Czech Republic). The enzymatic activity of tryptase released by human cultured mast cells (CHMCs) upon stimulation with IgE was quantified by cleavage of the synthetic fluorescent peptide substrate Z-Ala-Lys-Arg-7-amino-4-methylcoumarin (MP Biomedicals, Solon, Ohio, USA) in tryptase buffer. B-cell receptor-dependent Erk phosphorylation was measured in Ramos cells by intracellular FACS (anti-pT202/pY204-ERK1/2-AlexaFluor488; BD Biosciences). Cell proliferation assays were performed using A549 epithelial cells and H1299 lung carcinoma cells using nuclear staining to measure cell numbers (4'6-diamidino-2-phenylindole, dihydrochloride (DAPI; Invitrogen, Darmstadt, Germany)).

Growth factor-dependent protein phosphorylation was detected in HeLa cells by staining permeabilized cells with phospho-specific antibodies and quantified by chemiluminescence (Luminator, Wallac Multilabel Counter; Perkin Elmer). Akt phosphorylation was measured following insulin stimulation and EGFR phosphorylation was measured following EGF stimulation (Phospho-AKT, Cell signaling technology, Danvers, Mass.; 1 µM Insulin, Millipore, Billerica, Mass.; Phospho-EGFR, tyr1173, clone 53A3, Cell Signaling Technology; 200 ng/ml recombinant human EGF, PeproTech, Hamburg, Germany). Human umbilical vein endothelial cells (HUVECs) were stimulated with VEGF and VEGFR2 phosphorylation was assessed by ELISA (100 ng/ml VEGF165, R&D Systems; Rabbit anti-phospho-VEGFR2 mAb, Cell Signaling Technology).

Animals and Heterotopic Heart Transplantations:

Male Brown Norway (BN) and Lewis (Lew) rats weighing 350 g were purchased from Harlan (Indianapolis, Ind.) and were housed under conventional conditions. All animals were fed standard rat chow and water ad libitum and received humane care in compliance with the Principles of Laboratory Animal Care formulated by the National Society for Medical Research and the Guide for the care and Use of Laboratory Animals published by the National Institutes of Health (National Institutes of Health publication No. 85-23, revised 1985). Allogeneic (BN-to-Lew) and syngeneic (Lew-to-Lew) heterotopic heart transplantations were performed as described previously (Ono et al., *J. Thorac. Cardiovasc. Surg.* 57:225-229, 1969). In brief, rats were anaesthetized using 2% isoflurane. The donor received an intravenous bolus of 500 I.U. heparin. Cardiac arrest was achieved using 20 ml Bretschneider solution (Custodiol, Dr. F. Koehler Chemie, Bensheim, Germany). The aorta and the pulmonary artery of the donor heart were anastomosed by end-to-side-anastomosis to the abdominal aorta and vena cava inferior of the recipient, respectively. Heart-beating score was assessed directly after transplantation for each animal from score 0 (no palpable contraction) to 4 (strong and regular contraction). Only animals with beating scores of 4 were included into the study.

Immunosuppression and Study Design:

Compound I and Compound III were provided by Rigel (South San Francisco, Calif.) and Tacrolimus was provided by Astellas (Munich, Germany). All drugs were administrated orally each in two different concentrations: Compound I LD (15 mg/kg BID; n=6) and HD (60 mg/kg BID; n=6); Compound III LD (5 mg/kg BID; n=6) and HD (20 mg/kg BID; n=6); Tac LD (1 mg/kg QD; n=6) and HD (4 mg/kg QD; n=6). Administration of all drugs was performed every day at the same time points. Tacrolimus was applied only once a day (QD) every 24 hours. During administration of Compound I (BID) and Compound III (BID) a 12 hour pause was kept in between each drug application.

Five-day Study:

Lew recipients of heterotopic BN heart transplants were randomly assigned to their group. Animals were either left untreated (groups 1 and 2; see Table 1,5-day study) or received their group specific medication (groups 3-8; see Table 1,5-day study) by oral application. An untreated syngeneic transplant group Lew-Lew was generated as control.

Graft Survival Study:

BN-to-Lew heterotopic heart transplantations were performed. Recipient animals were treated for 10 days according to Table 1 (10 day survival study group) and graft survival was monitored by daily palpation of the beating donor heart through the abdominal wall. Scoring was assessed according to heart-beating score of 0 to 4. The time of rejection was defined as the last day of palpable cardiac contractions and graft rejection was confirmed by laparotomy.

TABLE 1

Study groups

| Group | Strain combination | Treatment | n |
|---|---|---|---|
| 5-day study groups | | | |
| 1 | BN-Lew | Control | 6 |
| 2 | BN-BN | Control | 6 |
| 3 | BN-Lew | Compound I LD (15 mg/kg) BID | 6 |
| 4 | BN-Lew | Compound I HD (60 mg/kg) BID | 6 |
| 5 | BN-Lew | Compound III LD (5 mg/kg) BID | 6 |
| 6 | BN-Lew | Compound III HD (20 mg/kg) BID | 6 |
| 7 | BN-Lew | Tac LD (1 mg/kg) QD | 6 |
| 8 | BN-Lew | Tac HD (4 mg/kg) QD | 6 |
| 10-day survival study groups | | | |
| 9 | BN-Lew | Control | 6 |
| 10 | BN-BN | Control | 6 |
| 11 | BN-Lew | Tac LD (1 mg/kg) QD | 6 |
| 12 | BN-Lew | Tac HD (4 mg/kg) QD | 6 |
| 13 | BN-Lew | Compound I LD (15 mg/kg) BID | 6 |
| 14 | BN-Lew | Compound I HD (60 mg/kg) BID | 6 |
| 15 | BN-Lew | Compound III LD (5 mg/kg) BID | 6 |
| 16 | BN-Lew | Compound III HD (20 mg/kg) BID | 6 |
| 17 | BN-Lew | Compound I LD (15 mg/kg BID + Tac LD (1 mg/kg) QD | 6 |
| 18 | BN-Lew | Compound III LD (5 mg/kg) BID + Tac LD (1 mg/kg) QD | 6 |

Histology and Immunohistochemistry:

Grafts were recovered five days after transplantation and fixed in 4% paraformaldehyde (Science Services, Munich, Germany), dehydrated and embedded in paraffin. The grafts were sliced into 3 µm thick cross sections and stained with hematoxylin and eosin (H+E; Waldeck, Carl Roth GmbH, Munster, Germany) and examined by standard light microscopy. The extent of acute cardiac graft rejection in H+E staining was examined by an experienced pathologist according to the 2004 ISHLT working formulation (Stewart et al., *J. Heart Lung Transplant.* 24:1710-1720, 2005).

Paraffin-embedded tissue sections were deparaffinized and rehydrated. Sections were incubated with protein blocking solution (ZytoChem Plus (AP) Polymer Kit; Zytomed Systems GmbH, Berlin, Germany) to prevent background staining. After antigen retrieval, specific antibodies against rat CD68 and CD3 (Serotec, Raleigh, N.C.) were applied to identify macrophages and lymphocytes, respectively, and visualized via alkaline phosphatase and new fuchsin substrate reaction (Zytomed System GmbH; Dako, Carpinteria, Calif.). Sections were counterstained by H+E (Waldeck). After overnight incubation with primary antibody solution and subsequent washing, enhancement reagent (ZytoChem) was applied, followed by enzymatic reaction of alkaline phosphatase induced by New Fuchsin Substrate System (Dako).

Inflammatory cell densities within the myocardium were assessed with the Leica QWin software (Leica Microsystems GmbH, Wetzlar, Germany) and expressed as cells/high-power field (HPF). Histological analyses of all stainings were done by a pathologist.

Quantibody Arrays:

Custom-made Cytokine Antibody Arrays (Raybiotech, Norcross, Ga.) were used to identify the expression profiles of intragraft cytokines IFN-γ, IL-10, and monocyte chemotactic protein (MCP)-1. Hearts were equally homogenized in 400 µl RIPA buffer (Sigma-Aldrich, St. Louis, Mo.). The protein content within the supernatant was quantified using the colorimetric BCA protein assay (Thermo Fisher Scientific, Rockford, Ill.) at 562 nm wavelength, according to the manufacturer's protocol. A total of 300 µg protein per Quantibody® array glass chip was used to quantitatively measure the intracellular cytokine content by ELISA in quadruplicates (Human cytokine array 1, Raybiotech). All values were normalized to the standard curve. Glass chip analysis was performed by Raybiotech.

Enzyme Linked Immune Spot Technique (ELISPOT):

Lymphocytes were isolated from freshly harvested spleens. ELISPOT assays with $1 \times 10^7$/ml mitomycin-inhibited BN splenocytes and $1 \times 10^6$/ml Lew splenocytes were performed according to the manufacturer's protocol (BD Biosciences). 96-well plates were coated with IFN-γ, IL-17, and IL-4 to assess T helper cell (Th)1-, Th17-, and Th2- responses independently. All assays were performed in quadruplicates. Spots were automatically enumerated using an ELISPOT plate reader (CTL, Cincinnati, Ohio) for scanning and analyzing.

Donor-specific Antibodies (DSA):

Donor splenocytes were isolated and erythrocytes were lysed using the ACK buffer (Lonza, Walkersville, Md.). Sera from recipient rats were decomplemented and equal amounts of sera and splenocyte suspensions ($5 \times 10^6$ cells/ml) were incubated for 30 minutes at room temperature. IgM antibodies were stained by incubation of the cells with a conjugated mouse antibody specific for the Fc-portion of rat IgM (Monoclonal Anti-rat IGM, Clone RTM-32, Sigma) followed by incubation with a 488-conjugated secondary antibody (Invitrogen). Cells were washed with PBS, fixed with 2% paraformaldehyde (Science Services), and analyzed on a FACSCalibur™ system (BD Biosciences). Fluorescence data were expressed as mean fluorescence intensity (MFI) using Flowjo software (Tree Star, Inc., Ashland, Oreg.).

Side Effects:

EDTA samples and sera were taken five days after transplantation for differential blood count, BUN, Creatinine, Cholesterol, HDL, LDL, Triglycerides, AST, and ALT, respectively. Analyses were performed by standard clinical chemistry procedures.

Combination Index (CI):

The median-effect principle of Chou (*in Synergism and Antagonism in Chemotherapy*, Chou and Rideout, eds, pp. 61-102, Academic Press, 1991) is based on the premise that the effect of each agent is related to its dose and, therefore, can be calculated using the following equation: (fa/fu)=(D/Dm) m, where fa and fu represent the fractions of the system that are affected (% inhibition or rather days of survival beyond controls) and unaffected (1−fa), respectively, by the drug at dose D. Full protection (fa=1) is defined as at least a 28-day survival of allografts. Dm is the dose required for 50% inhibition ($ED_{50}$), the median effect (m) is a coefficient that describes the sigmoidicy of the dose-effect curve. The interaction between two drugs is assessed by the combination index (CI) equation for the doses to achieve x % inhibition:

$$CI_x = \frac{D_1 combined}{D_1 alone} + \frac{D_2 combined}{D_2 alone} + \frac{(D_1 combined)(D_2 combined)}{(D_1 alone)(D_2 alone)}$$

for the mutually nonexclusive case, where each drug has a different mode of action. A computer software program was used to determine the dose-effect parameters (Dm, m, and r), and the CI values (CalcuSyn, Biosoft, Cambridge, United Kingdom).

Statistical Analyses:

Data are presented as mean±standard deviation (SD). Comparisons between groups were done by analysis of variance between groups (ANOVA) with Least Significant Difference post hoc tests. Probability values (p) of less than 0.05 were considered significant. Statistical analyses were performed using the SPSS statistical software package 17.0 for Windows (SPSS Inc., Chicago, Ill.).

Example 2

Pharmacokinetics and Pharmacodynamics

Pharmacokinetics were performed in male Lewis rats. Plasma levels were measured within a 10 hour period. Resulting plasma concentrations of Compound I HD (60 mg/kg BID), Compound I LD (15 mg/kg BID), Compound III HD (20 mg/kg BID), and Compound III LD (5 mg/kg BID) are depicted in FIG. 1. Compound I HD and Compound I LD plasma levels peaked 1.5-2 hours after administration. Compound III HD plasma levels peaked after 3-3.5 hours and Compound III LD levels 2 hours after administration. Area under the concentration-time curve (AUC) in the Compound I HD dosage group was >13-fold higher than that for Compound I LD. Plasma levels in Compound III HD group resulted in >22-fold higher AUC compared to Compound III LD dosage.

Compound III and Compound I were identified as potent small molecule inhibitors of JAK1/3 kinases in a screen for inhibitors of IL-2 signaling in primary human T-cells. Table 2 lists the potencies of Compound III and Compound I in a panel of JAK-dependent and non-JAK dependent cell-based assays along with a pan-JAK inhibitor (Compound IV) for comparison. Compound III and Compound I inhibited JAK1/3-dependent Stat5 phosphorylation in response to IL-2 with $EC_{50}$s of 35 nM and 21 nM respectively, and blocked the resulting T-cell proliferation with similar $EC_{50}$s. Consistent with this, Compound III and Compound I also potently inhibited the proliferative response of human primary T-cells to dendritic cell costimulation in the mixed lymphocyte reaction (MLR) with $EC_{50}$s of 22 nM and 16 nM, respectively. In human primary T-cells, Compound III and Compound I also inhibited JAK1/Tyk2-dependent phosphorylation of Stat1 in response to IFN-γ, but only weakly inhibited JAK2/Tyk2-dependent phosphorylation of Stat4 in response to IL-12. Furthermore, Compound III and Compound I showed limited inhibition of JAK2-dependent cord blood derived human erythroid progenitor cell (CHEP) differentiation and survival in response to erythropoietin (EPO), as well as JAK1/2-dependent ICAM-1 expression in U937 cells in response to IFN-γ. Taken together, this data shows that Compound III and Compound I are potent inhibitors of JAK1 and JAK3 kinases with 20-fold or more selectivity over JAK2 and Tyk2 kinases in cells. In contrast, Compound IV is a pan-JAK inhibitor and potently inhibits JAK2 and Tyk2 signaling (EPO and IL-12) as well as JAK1 and JAK3 signaling (IL-2 and IFN-γ). The JAK kinase selectivity of the inhibitors was also assessed in whole blood assays. While the potency of the compounds was significantly reduced in blood, likely due to serum protein binding or red blood cell partitioning, the selective inhibition of IL-2 and IFN-γ signaling was retained.

The compounds were further profiled in a panel of cell-based assays to assess their activity against a range of kinase targets, including cytoplasmic tyrosine kinases such as Syk, Lck, ZAP-70, and the receptor tyrosine kinases, VEGFR, INSR and EGFR, as well as a multitude of serine threonine kinases involved in signaling downstream of these receptors and receptor-proximal kinases (for example, PI3-kinase pathway, MAPK pathways, PKC and NFκB pathways). Compound III and Compound I showed very limited inhibition of all of these other kinase targets in cells.

TABLE 2

Effect of Compound I and Compound III in cell-based assays.

| Assay | Upstream Kinases | EC50 (μM) | | |
|---|---|---|---|---|
| | | Compound III | Compound I | Compound IV (pan-JAK) |
| MLR | | 0.022 ± 0.006 | 0.016 ± 0.007 | 0.005 (n = 1) |
| JAK kinase-dependent cell-based activity | | | | |
| IL-2 T cell proliferation | JAK1/3 | 0.030 ± 0.013 | 0.021 ± 0.007 | 0.022 ± 0.009 |
| IL-2 T cell phospho-STAT5 | JAK1/3 | 0.035 ± 0.015 | 0.021 ± 0.009 | 0.026 ± 0.016 |
| IFN-γ T cell phospho-STAT1 | JAK1/Tyk2 | 0.007 ± 0.001 | 0.009 ± 0.007 | 0.002 ± 0.0005 |
| IL-12 T cell phospho-STAT4 | JAK2/Tyk2 | 1.564 ± 0.971 | 0.463 (n = 1) | 0.094 ± 0.067 |
| IFN-γ U937 ICAM-1 | JAK1/2 | 0.791 ± 0.352 | 0.417 ± 0.211 | 0.041 ± 0.028 |
| EPO CHEP Survival | JAK2 | 1.111 ± 0.339 | 0.490 ± 0.246 | 0.099 ± 0.055 |
| Non-JAK-dependent cell-based activity | | | | |
| Anti-CD3/CD28 T cell IL-2 production | Lck/AZP70 | 19.73 ± 2.90 | 2.865 ± 0.118 | 0.514 (n = 1) |

TABLE 2-continued

Effect of Compound I and Compound III in cell-based assays.

| Assay | Upstream Kinases | EC50 (µM) | | |
|---|---|---|---|---|
| | | Compound III | Compound I | Compound IV (pan-JAK) |
| IgE CHMC tryptase | Syk | 0.380 ± 0.150 | 0.457 ± 0.263 | 0.239 ± 0.142 |
| Anti-IgM Ramos phospho-Erk | Syk | 1.281 ± 0.190 | 1.441 ± 0.586 | ND |
| A549 proliferation | Multiple | 5.418 ± 3.040 | 1.862 ± 0.251 | 1.969 ± 0.648 |
| H1299 proliferation | Multiple | 5.085 ± 1.820 | 3.430 ± 1.307 | 3.966 ± 1.341 |
| VEGF HUVEC phospho-VEGFR2 | VEGFR2 | 29.30 ± 14.28 | 17.77 ± 3.87 | 2.87 (n = 1) |
| Insulin HeLa phospho-Akt | INSR | Inactive | Inactive | ND |
| EGF HeLa phospho-EGFR | EGFR | Inactive | Inactive | ND |
| Whole blood activity | | | | |
| IL-2 whole blood lymphocytes phospho-STAT5 | JAK1/3 | 0.887 ± 0.295 | 0.416 ± 0.152 | 0.260 ± 0.135 |
| IFN-γ whole blood lymphocytes phospho-STAT1 | JAK1/Tyk2 | 0.511 ± 0.279 | 0.153 ± 0.033 | 0.086 ± 0.055 |
| IL-6 whole blood lymphocytes phospho-STAT3 | JAK1/2/Tyk2 | 6.690 ± 1.61 | 3.833 ± 1.522 | 1.287 ± 0.936 |
| GM-CSF whole blood granulocytes phospho-STAT5 | JAK2 | >50 | 32.7 ± 9.51 | 0.801 ± 0.608 |

ND, not determined

Example 3

Five Day Allograft Study

Figure 2A:
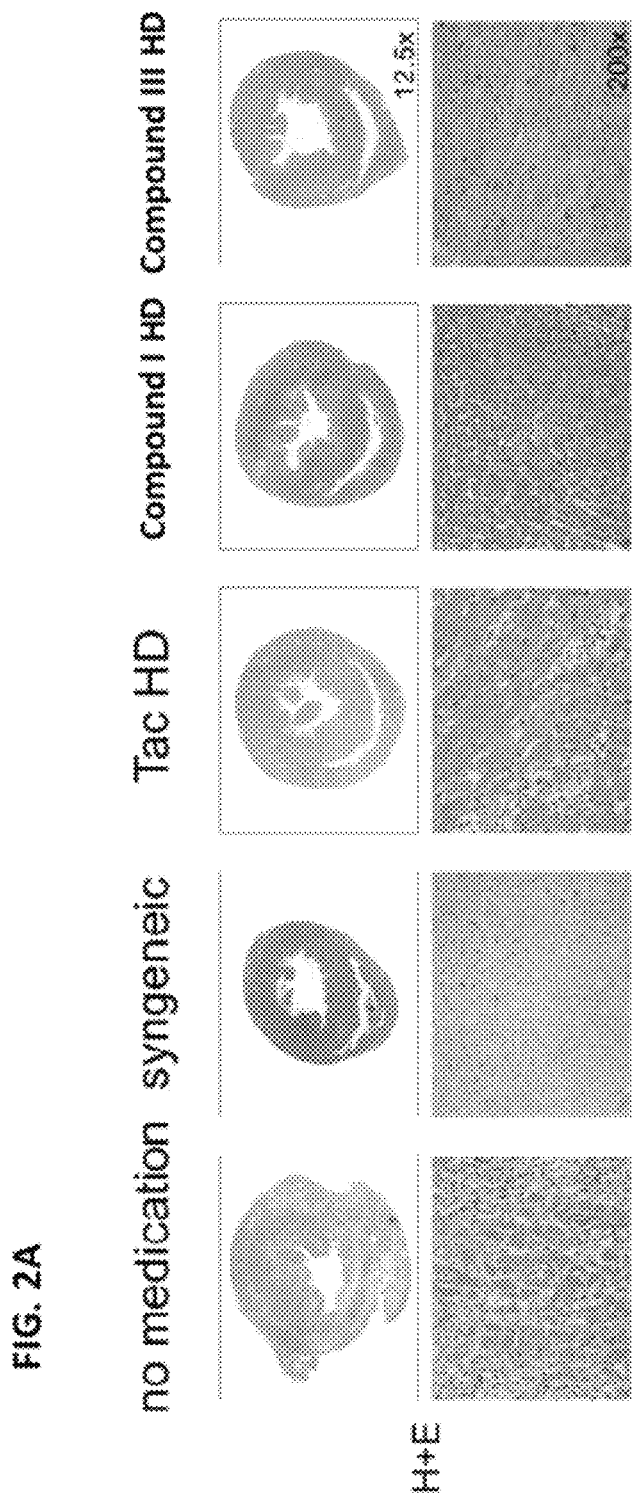
FIG. 2A is a series of digital images showing hematoxylin and eosin (H+E) staining of midgraft cross sections from the indicated treatment groups five days after transplantation. Upper panel, 12.5× magnification; lower panel 200× magnification.

Five days after transplantation, H+E stained cross-sections of harvested syngeneic hearts showed no pathological signs of rejection, such as myocyte necrosis, edema, hemorrhages and vasculitis (FIG. 2A). The no medication group showed the highest grade of destroyed myocardial tissue, massive mononuclear cell infiltration and destruction of myocyte architecture (FIG. 2A). In contrast to the no medication group, all medication groups presented less diverse grades of cellular infiltration and modification of tissue morphology (FIG. 2A).

Figure 2B:
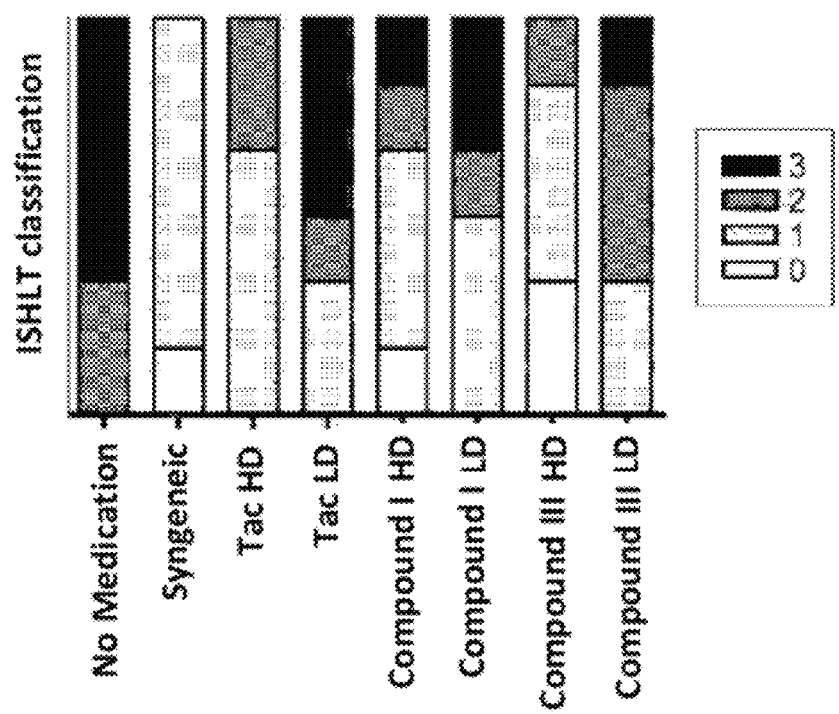
FIG. 2B is a graph showing the distribution of rejection classes according to the revised ISHLT classification in the indicated treatment groups five days after transplantation.

Resulting ISHLT 2004 classification (Stewart et al., *J. Heart Lung Transplant.* 24:1710-1720, 2005) is depicted in FIG. 2B. The no medication group showed 67% of scored hearts with an ISHLT score of 3, and 33% with an ISHLT score of 2. Histological H+E staining indicated a massive breaking-up of heart tissue structure. The syngeneic Lew-to-Lew group demonstrated 83% of hearts with an ISHLT score of 1, and 17% with a score of 0. In comparison to the no medication group, H+E staining of the syngeneic group showed a homogeneous and coherent heart tissue. Tacrolimus HD medication resulted in 33% with an ISHLT score of 2, and 67% with an ISHLT score of 1. Compound I HD treatment resulted in 17% with an ISHLT score of 3, 17% with a score of 2, 50% with a score of 1 and 17% with a score of 0. Compared between the three HD medication groups, the Compound III HD medication group showed the best results with no scores of 3, 17% with an ISHLT score of 2, 50% with a score of 1, and 33% with a score of 0. A dose-dependent effect was observed for all medication groups.

Figure 2C:
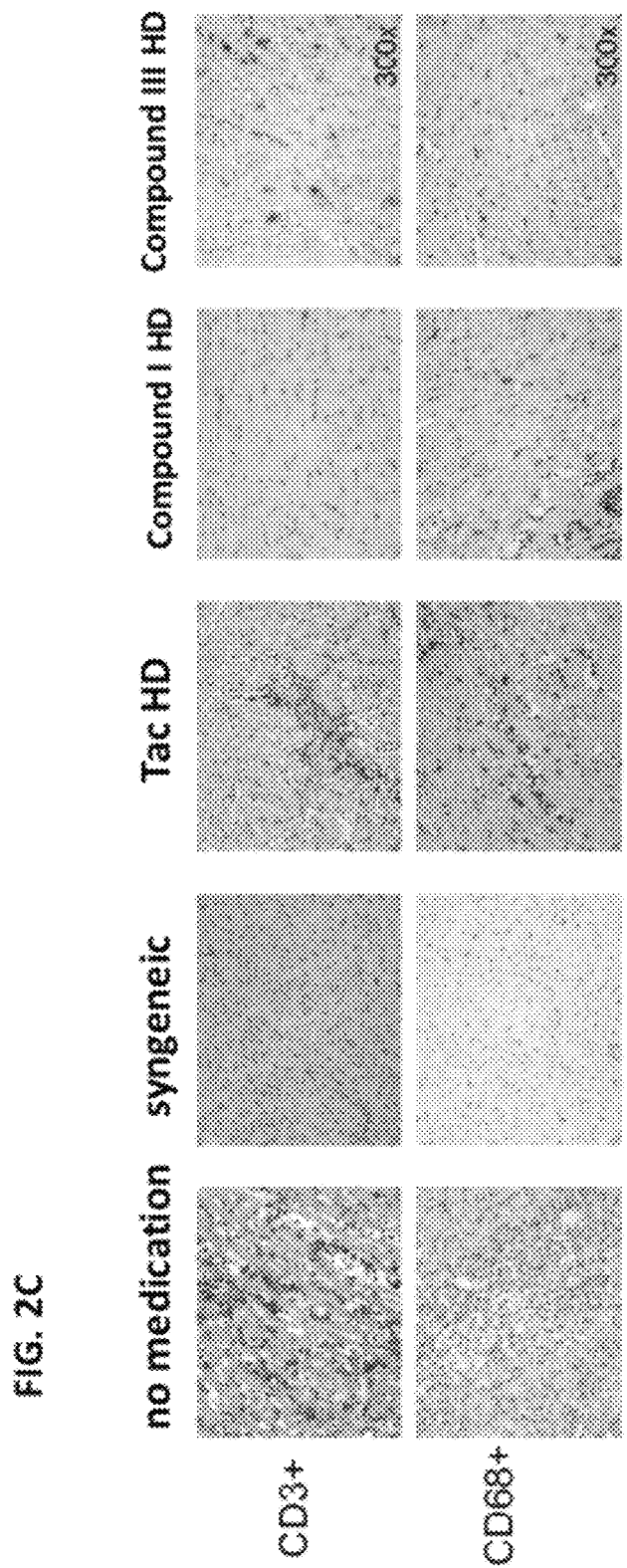
FIG. 2C is a series of digital images showing immunohistochemistry for CD3+ lymphocytes (upper) and CD68+ macrophages (lower) in midgraft cross-sections from the indicated treatment groups five days after transplantation (300× magnification).
Figure 2D:
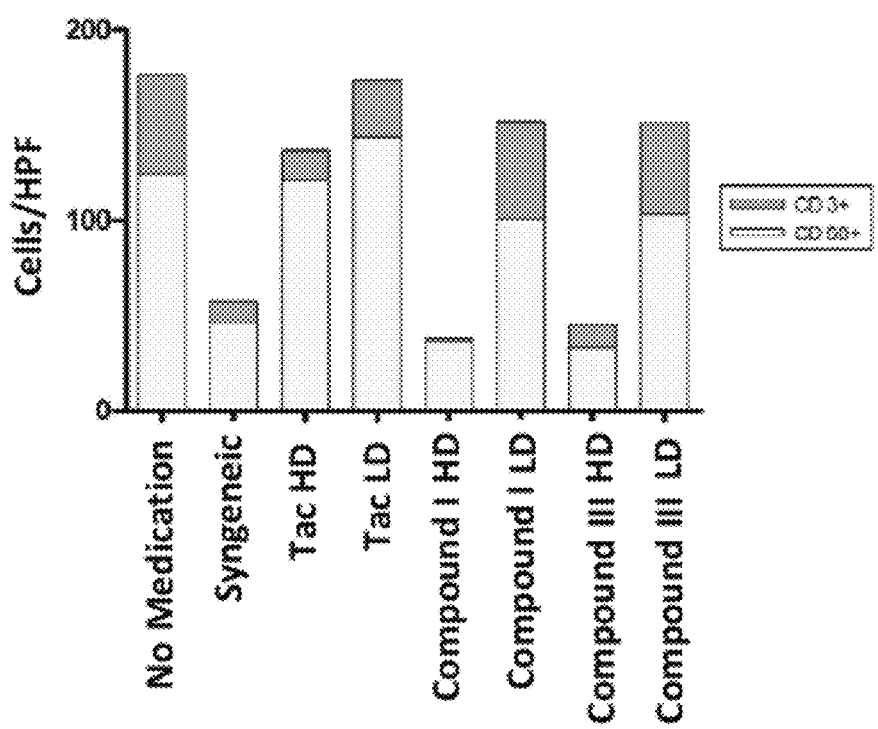
FIG. 2D is a graph showing the number of CD3+ and CD68+ cells/high power field in the sections shown in FIG. 2C.

Further quantification of mononuclear cell infiltration was evaluated by immunohistochemistry, identifying CD3+ lymphocytes and CD68+ macrophages (FIGS. 2C and 2D). Massive CD3+ and even more CD68+ cell infiltrations were observed in the no medication group. As opposed to the no medication group, the heart tissue of the syngeneic group showed significantly less CD3+ and CD68+ cell infiltration ($p<0.001$).

All three high dose treatment groups showed a significant decrease of CD3+ cell infiltration compared to no medication group ($p<0.001$) and CD68+ cells were significantly reduced in Compound I HD and Compound III HD medication group compared to no medication groups ($p<0.001$). Compound I HD and Compound III HD treatment resulted in significantly less CD68+ cell infiltration compared to the Tac HD medication group ($p<0.001$). Furthermore, Compound I LD and Compound III LD treatment resulted in less CD68+ and CD3+ cell infiltration compared to the Tac LD group ($p<0.05$).

Figure 3A:
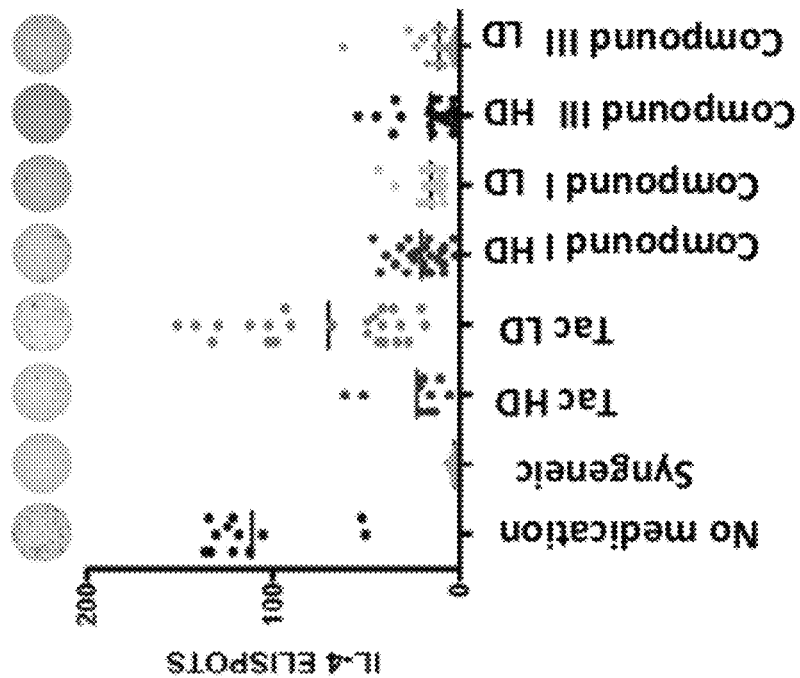
FIG. 3A is a graph showing ELISPOT assay results for interferon (IFN)-γ in the indicated treatment groups five days after transplantation.

Mitomycin-inhibited donor cells were incubated with recipient cells five days after transplantation. The no medication group showed a strong cellular IFN-γ release against donor antigens. Whereas only slight IFN-γ spots were observed in the syngeneic group compared to the no medication group ($p<0.001$), IFN-γ spot frequency was significantly reduced in all HD treatment groups, as well as in the Compound I LD and Compound III LD groups compared to the no medication group ($p<0.001$; FIG. 3A). Compound I LD and Compound III LD treatment showed significantly better results in suppressing IFN-γ response to donor-specific antigens compared to Tac LD treatment ($p<0.001$). Tac LD showed no significant reduction of IFN-γ spot frequency compared to the no medication group. Treatment with Compound I LD and HD, as well as Tac LD and HD, showed dose-dependent effects on Th1 cells (Tac HD vs. LD: $p<0.001$; Compound I HD vs. LD: $p<0.001$). Compound III LD treatment resulted in less IFN-γ spot frequency compared to the Tac HD group (p<0.05).

Figure 3B:
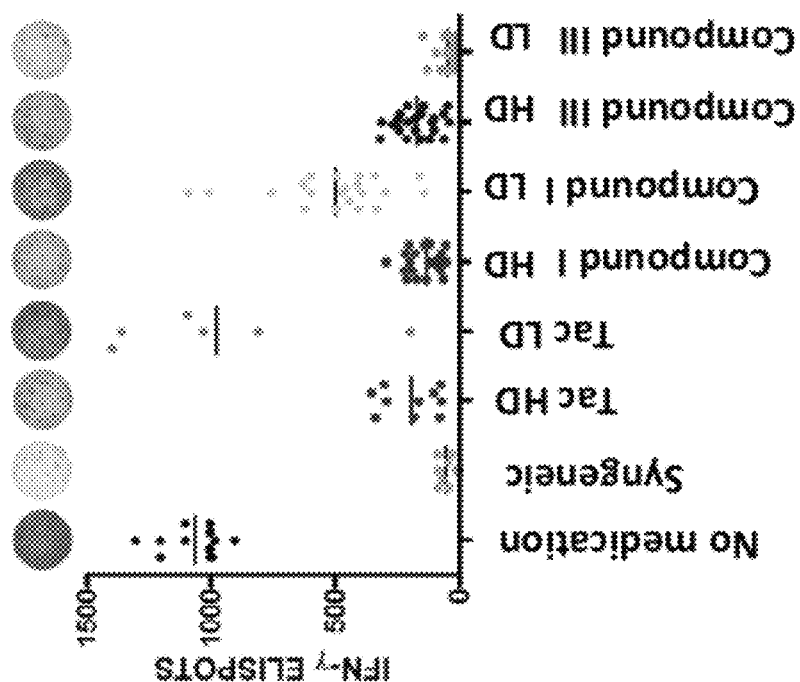
FIG. 3B is a graph showing ELISPOT assay results for interleukin (IL)-4 in the indicated treatment groups five days after transplantation.
Figures 3C, 3D:
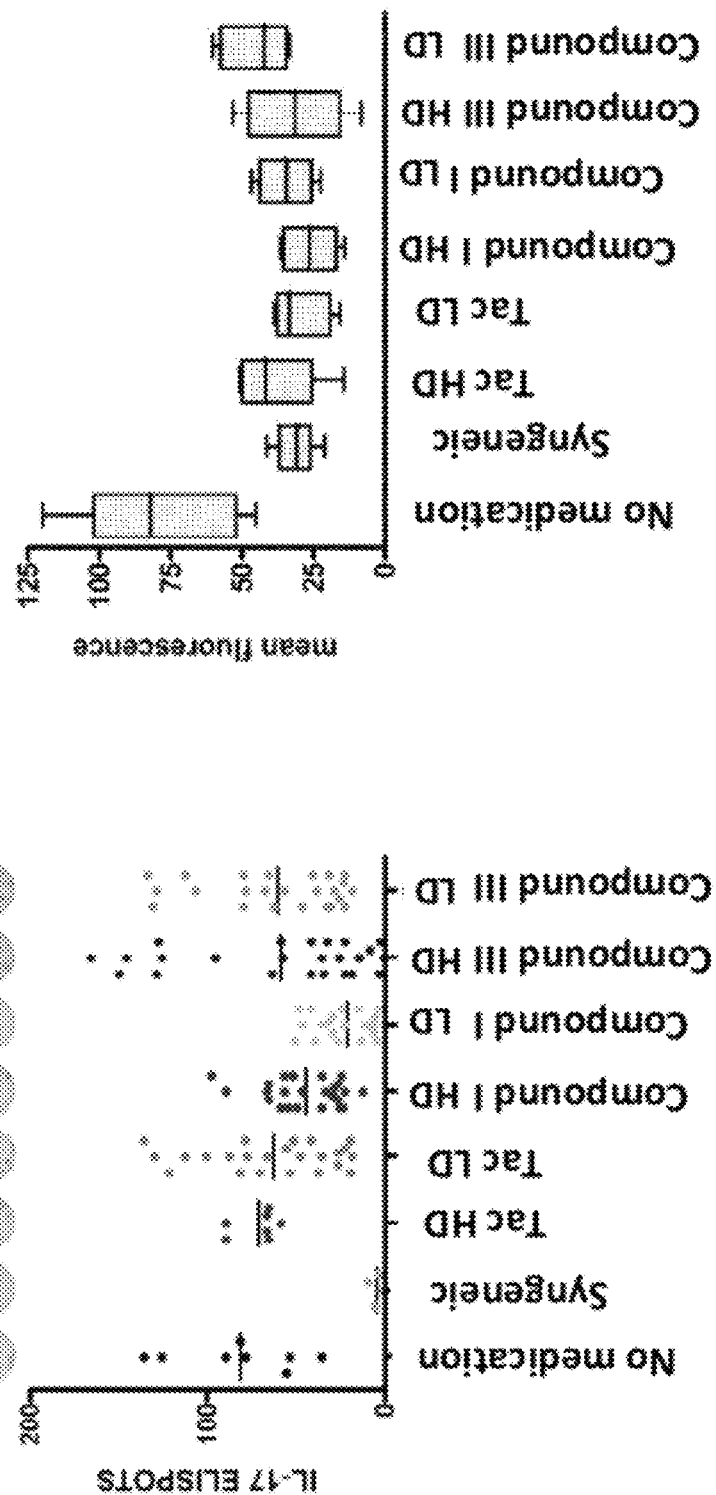
FIG. 3C is a graph showing ELISPOT assay results for IL-17 in the indicated treatment groups five days after transplantation.
FIG. 3D is a graph showing mean fluorescence of donor specific alloantibodies stained for the Fc region of IgM and detected by flow cytometry (n=6) five days after transplantation. All groups showed significant suppression of alloreactive antibody production (p<0.001, Compound I/Compound III/Tac vs. no treatment).

The same trend was visible for IL-4 release of Th2 cells (FIG. 3B). All treatment groups significantly diminished the cytokine release compared to the no medication group (p<0.0011). All HD treatment groups showed similar potency in suppressing systemic Th2-response. However, the JAK1/3 inhibitors in LD treatment groups significantly decreased IL-4 spot frequency compared to Tac LD treatment (p<0.001). IL-17 cytokine release was significantly suppressed by Compound I HD and Compound I LD groups compared to the no medication group (Compound I HD p<0.010; R %07 LD p<0.001; FIG. 3C). Compound I LD resulted in significantly less spot frequency compared to Tac LD (p<0.001).

DSA were measured by flow cytometry five days after transplantation. Quantification of DSA showed significantly decreased IgM antibodies in all LD and HD medication groups (p<0.001 vs. no medication; FIG. 3D). All groups showed dose dependent effects of DSA suppression. Although suppression of DSA in the Compound I and Compound III treatment groups was not significantly better compared to the Tac treatment groups, the mean values of fluorescence were less in the Compound I and Compound III medication groups compared to the Tac treatment groups.

Figure 4:
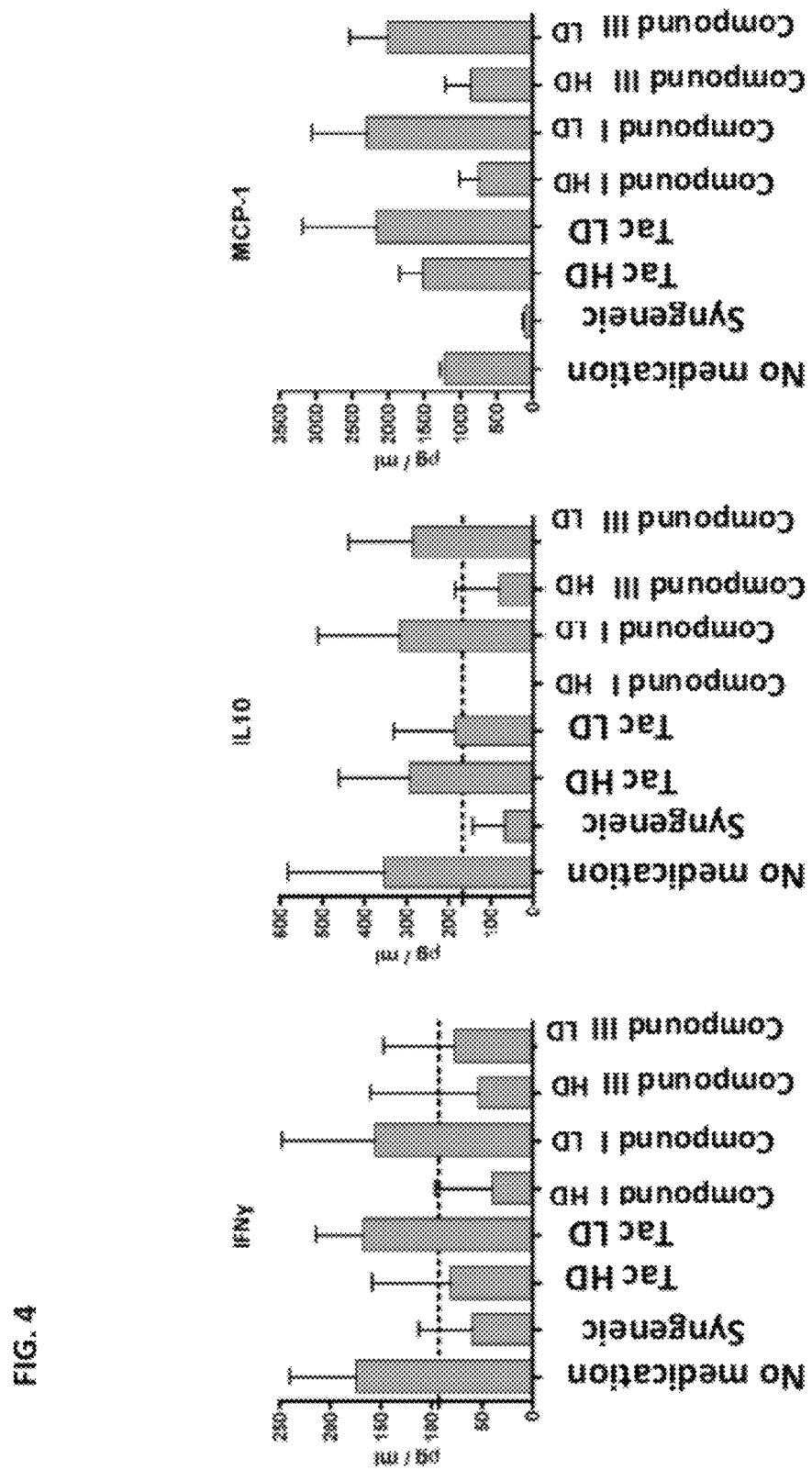
FIG. 4 is a series of graphs showing intragraft IFN-γ (left), IL-10 (middle), and monocyte chemotactic protein (MCP)-1 (right) release five days after transplantation. Compound I and Compound III HD groups showed significant reduction of IFN-γ and IL-10 release (p<0.05). MCP-1 response was not significantly reduced in all treatment groups compared to the no treatment group.

Intragraft quantification of cytokine release was performed five days after transplantation. FIG. 4 (left panel) demonstrates the release of IFN-γ by natural killer, natural killer T cells, CD4+ T helper cells, and CD8+ cytotoxic T lymphocytes. Intragraft IFN-γ release was significantly less in the Compound I HD and Compound III HD medication groups (p<0.05). The graph in FIG. 4 (middle panel) demonstrates the monocytic and lymphocytic IL-10 release, which was significantly reduced in the two groups treated with Compound I HD or Compound III HD, compared to no medication group (p<0.05). Moreover, Compound I HD and Compound III HD resulted in significantly less IL-10 release compared to Tac HD treatment (p<0.05; FIG. 4). MCP-1 release, by monocytes, macrophages and dendritic cells, showed no significant differences in the treatment groups compared to the no medication group (FIG. 4, right panel). Nevertheless, treatment with Compound I HD and Compound III HD demonstrated lower mean values of MCP-1 release compared to Tac HD treatment.

No obvious signs of discomfort, such as diarrhea or neurological dysfunction were observed in any animals during or after the treatment period. No pathological changes in the hematopoietic system were observed in EDTA blood samples. In addition, BUN, Creatinine, Cholesterol, LDL, HDL, Triglycerides, AST, and ALT were measured in serum samples. Total cholesterol was similar in all treatment groups. Tac HD, Compound I HD, Compound I LD, and Compound III HD showed positive effects in the lipid profile in increased HDL values compared to the no medication group (mean 46.7 mg/dl, mean 50.2 mg/dl, mean 41.2 mg/dl, mean 46.3 mg/dl, and mean 26.0 mg/dl, respectively) (p<0.003, p<0.001, p<0.038, and p<0.003, respectively). LDL levels were decreased in Tac HD, Tac LD, Compound I HD, and Compound III LD compared to the no medication group (mean 9.9 mg/dl, mean 7.5 mg/di, mean 8.7 mg/dl, mean 19.6 mg/dl, respectively) (p<0.03, p<0.006, p<0.011, and p=0.019, respectively).

Serum levels of AST and ALT were assessed to assess hepatotoxic side effects in the medication groups. All medication groups, except sub-therapeutic tacrolimus treatment in the Tac LD group, showed elevation of serum ALT compared to the no medication group and syngeneic group (p<0.05). Serum AST levels remained unaffected in all groups.

Example 4

Long-Term Survival Study

Graft survival was monitored by daily palpation of the beating donor heart through the abdominal wall and treatment of animals was stopped after 10 days.

Figure 5:
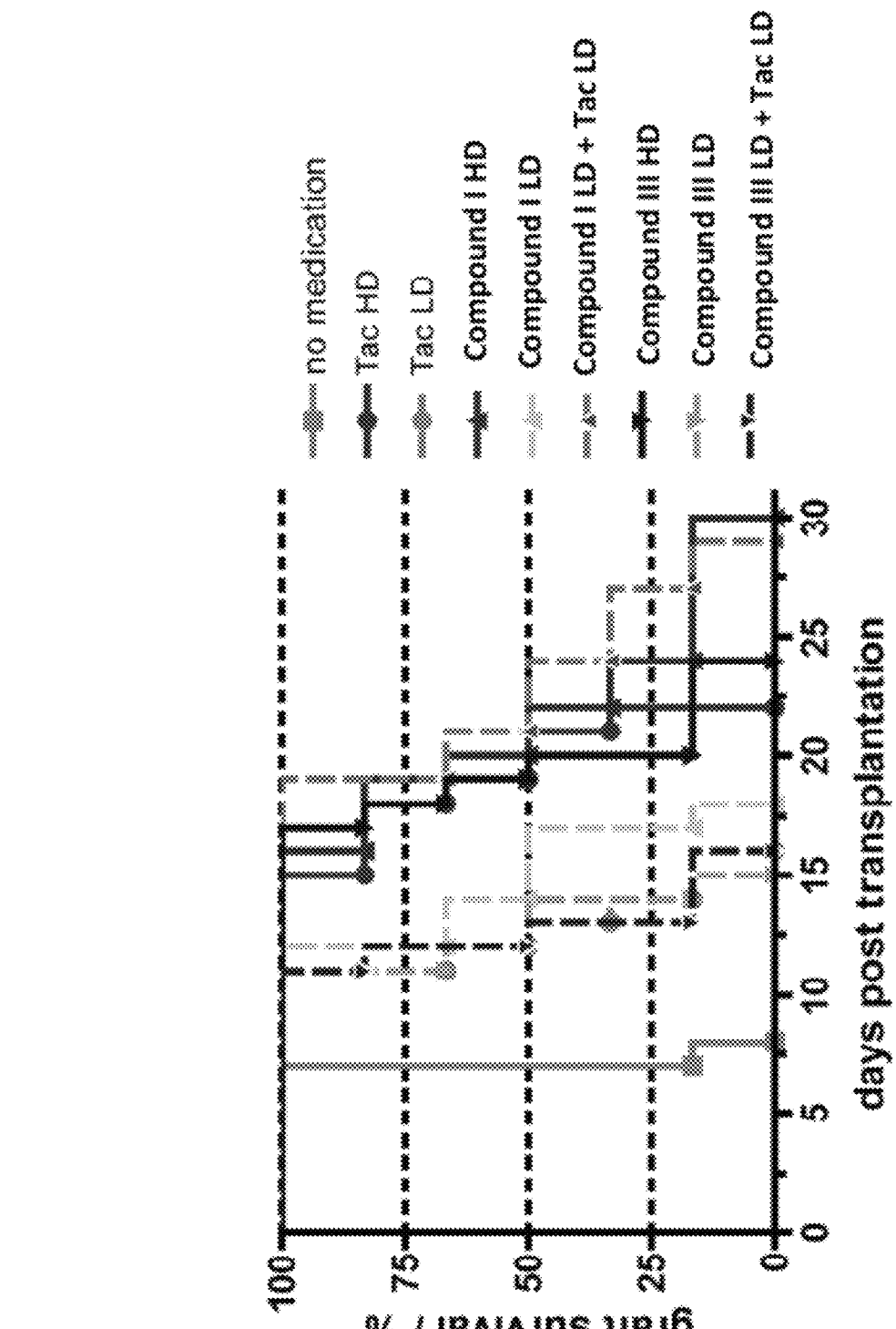
FIG. 5 is a plot showing graft survival after a 10-day treatment period with the indicated compound or combination. Grafts were scored by daily abdominal palpitation of transplanted hearts. Hearts were defined as rejected when they reached a score of 0. ■=no medication group; ●, solid line=Tac HD group; ●, dotted line=Tac LD group; ▲, solid line=Compound I HD group; ▲, light dotted line=Compound I LD group; ▲, dark dotted line=Compound I LD+Tac LD group; ▼, solid line=Compound III HD group; ▼, light dotted line=Compound III LD group; ▼, dark dotted line=Compound III LD+Tac LD group.

Graft survival was significantly prolonged in the Tac LD and Compound III LD treatment groups compared to the no medication group (13±2 days, 13±2 days, 7±0 days, respectively) (p<0.05) (FIG. 5). Compound I LD treatment resulted in longer survival compared to no medication (15±3 days, 7±0 days, respectively) (p<0.001). All HD medication groups prolonged graft survival significantly better compared to the no medication and LD treatment groups (Tac HD, 20±3 days; Compound I HD, 22±5 days; Compound III HD, 20±4 days) (p<0.001). Dose dependent effects were observed, while best results were achieved by Compound I HD treatment. Both Compound I HD and Compound III HD showed similar efficacy to preserve cardiac allograft function in vivo, resulting in mean survival days of 22±5 days and 20±2 days, respectively, compared to 7±0 days in the no medication group (p<0.001) and 20±3 days in the Tac HD treatment group.

The results of combination regimens of Compound I LD and Compound III LD with Tac LD are shown in FIG. 5. The combination of Compound I LD with Tac LD was as effective as Compound I HD monotherapy (mean survival of 22±5 and 22±6 days, respectively). Compared to the single-drug regimens of Compound I LD or Tac LD, the graft survival was significantly prolonged (p<0.001). The resulting Combination Index of 0.584 showed synergistic effects in combination of Compound I LD with Tac LD medication. Combination of Compound III LD with Tac LD resulted in mean survival of 13±2 days, which was the same as for the single regimen of Compound III LD medication. There was also no benefit seen in combination regimens of Compound III LD with Tac LD compared to single regimens of Tac LD treatment. Calculation of the Combination Index resulted in 3.0, which indicates an antagonistic effect of Compound III LD and Tac LD in combination treatment.

Example 5

Methods of Treating or Inhibiting Allograft Rejection

This example describes exemplary methods for treating or inhibiting allograft rejection in a transplant recipient with a JAK1/3 inhibitor and a non-JAK1/3 inhibitor immunosuppressant. However, one skilled in the art will appreciate that methods that deviate from these specific methods can also be used to successfully treat or inhibit allograft rejection in a transplant recipient.

Based on the teachings disclosed herein, allograft rejection can be treated or inhibited in a transplant recipient by administering to the transplant recipient the JAK1/3 inhibitor Compound I or a prodrug thereof and the non-JAK1/3 inhibitor immunosuppressant calcineurin inhibitor tacrolimus.

In one example, a clinical trial includes half of the subjects following an established protocol for treating or inhibiting allograft rejection (such as tacrolimus). The other half is treated by administering a JAK1/3 inhibitor including Compound I or a prodrug thereof and tacrolimus. In some examples, the subject is a transplant recipient (such as a subject who has received a heart, lung, liver, or kidney transplant).

A first amount of the JAK1/3 inhibitor Compound I, or its prodrug (Compound II) and a second amount of tacrolimus is administered to the transplant recipient (such as a subject who has received or will receive a heart, lung, liver, or kidney transplant). Administration of Compound I (or Compound II) and tacrolimus can be achieved by any method known in the art, such as oral, inhalation, intravenous, intramuscular, intraperitoneal, or subcutaneous administration. In some examples, Compound I or Compound II and tacrolimus are each administered orally.

The amount of the JAK1/3 inhibitor Compound I, or its prodrug (e.g., Compound II) and tacrolimus depends on the subject being treated, the type of transplant the subject has or will receive, and the manner of administration of the therapeutic composition. Ideally, a therapeutically effective amount of each agent is the amount of each that in combination is sufficient to prevent, reduce, inhibit, and/or treat the condition (e.g., allograft rejection) in the transplant recipient without causing a substantial cytotoxic effect in the subject. The effective amounts can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily or twice daily repeated administration protocol, as appropriate for each compound). Administration of the therapeutic compositions can be taken long term (for example over a period of months or years).

Following the administration of Compound I (or prodrug thereof) and tacrolimus, the transplant recipient is monitored for presence or severity of allograft rejection (such as graft versus host disease or graft fibrosis). In particular examples, subjects are analyzed one or more times, for example starting 1 month after start of treatment. Subjects can be monitored using any method known in the art. For example, acute allograft rejection can be assessed by biopsy of the allograft. Patient and graft survival can also be assessed, for example at 6 and 12 months post-transplantation. A reduction in the presence or severity of symptoms associated with allograft rejection indicates the effectiveness of the treatment.

One of skill in the art will appreciate that combination therapy of Compound I (or a prodrug thereof, such as Compound II) and tacrolimus can be tested for safety in animals, and then used for clinical trials in animals or humans. In one example, animal models of allogeneic transplantation are employed to determine therapeutic value and appropriate dosages of the disclosed agents.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of inhibiting or treating allograft rejection in a transplant recipient, comprising:
administering to the transplant recipient a first amount of a JAK1/3 inhibitor comprising 5-(2-(4-fluoro-3-methoxy-5-methylphenylamino)-5-methylpyrimidin-4-ylamino)benzo[d]oxazol-2(3H)-one or a prodrug thereof; and
administering to the transplant recipient a second amount of a non-JAK1/3 inhibitor immunosuppressant, wherein the combined effect of the first amount and the second amount is greater than the effect of the first amount or the second amount individually, wherein the JAK1/3 inhibitor acts in combination with the non-JAK1/3 inhibitor immunosuppressant to inhibit or treat allograft rejection.

2. The method of claim 1, wherein the combined effect of the first amount and the second amount is synergistic.

3. The method of claim 1, wherein at least one of the first amount and the second amount is individually a suboptimal dose for inhibiting or treating allograft rejection in the transplant recipient.

4. The method of claim 1, wherein the non-JAK1/3 inhibitor immunosuppressant comprises a calcineurin inhibitor, an inhibitor of mTOR, an inhibitor of inosine monophosphate dehydrogenase (IMPDH), an anti-T-cell antibody, or a combination of two or more thereof.

5. The method of claim 4, wherein the non-JAK1/3 inhibitor immunosuppressant comprises a calcineurin inhibitor.

6. The method of claim 5, wherein the calcineurin inhibitor comprises tacrolimus, cyclosporine, or pimecrolimus.

7. The method of claim 6, wherein the calcineurin inhibitor is tacrolimus.

8. The method of claim 1, wherein the prodrug comprises sodium-(5-(2-(4-fluoro-3-methoxy-5-methylphenylamino)-5-methylpyrimidin-4-ylamino)-2-oxobenzo[d]oxazol-3(2H)-yl)methyl phosphate.

9. The method of claim 1, wherein the transplant recipient is a subject who has received a heart transplant, a lung transplant, a liver transplant, or a kidney transplant.

10. The method of claim 1, wherein the allograft rejection comprises hyperacute rejection, acute rejection, or chronic rejection.

11. The method of claim 1, wherein 5-(2-(4-fluoro-3-methoxy-5-methylphenylamino)-5-methylprrimidin-4-ylamino)benzo[d]oxazol-2(3H)-one or a prodrug thereof and the non-JAK1/3 inhibitor immunosuppressant are administered to the transplant recipient sequentially or simultaneously.

12. The method of claim 1, wherein administering the JAK1/3 inhibitor comprises administering about 15 mg/kg of 5-(2-(4-fluoro-3-methoxy-5-methylphenylamino)-5-methylpyrimidin-4-ylamino)benzo[d]oxazol-2(3H)-one to the transplant recipient.

13. The method of claim 1, wherein administering the non-JAK1/3 inhibitor immunosuppressant comprises administering about 1 mg/kg tacrolimus to the transplant recipient.

14. The method of claim 1, wherein administering the non-JAK1/3 inhibitor immunosuppressant comprises administering a series of tapered doses of the non-JAK1/3 inhibitor immunosuppressant to the transplant recipient.

15. The method of claim 14, wherein the series of tapered doses is administered as a series of doses following a linear taper of about 10-25%.

16. The method of claim 1, wherein administering the JAK 1/3 inhibitor to the transplant recipient comprises administering the JAK1/3 inhibitor to a tissue or organ prior to transplanting the tissue or organ in the transplant recipient.

17. A method of inhibiting or treating allograft rejection in a transplant recipient, comprising:
administering to the transplant recipient a first amount of a JAK1/3 inhibitor comprising 5-(2-(4-fluoro-3-methoxy-5-methylphenylamino)-5-methylpyrimidin-4-ylamino)benzo[d]oxazol-2(3H)-one or a prodrug thereof; and administering to the transplant recipient a second amount of a non-JAK1/3 immunosuppressant, wherein at least one of the first amount and the second amount is individually a suboptimal dose for inhibiting or treating allograft rejection in the transplant recipient, and wherein the combined effect of the first amount and the second amount is greater than the effect of the first amount or the second amount individually, wherein the JAK1/3 inhibitor acts in combination with the non-JAK1/3 inhibitor immunosuppressant to inhibit or treat allograft rejection.

18. The method of claim 17, wherein the combined effect of the first amount and the second amount is synergistic.

19. The method of claim 17, wherein the non-JAK1/3 inhibitor immunosuppressant comprises a calcineurin inhibitor, an inhibitor of mTOR, an inhibitor of inosine monophosphate dehydrogenase (IMPDH), an anti-T-cell antibody, or a combination of two or more thereof.

20. The method of claim 19, wherein the non-JAK1/3 inhibitor immunosuppressant comprises a calcineurin inhibitor.

21. The method of claim 20, wherein the calcineurin inhibitor comprises tacrolimus, cyclosporine, or pimecrolimus.

22. The method of claim 21, wherein the calcineurin inhibitor is tacrolimus.

23. The method of claim 17, wherein the prodrug comprises sodium-(5-(2-(4-fluoro-3-methoxy-5-methylphenylamino)-5-methylpyrimidin-4-ylamino)-2-oxobenzo[d]oxazol-3(2H)-yl)methyl phosphate.

24. The method of claim 17, wherein the transplant recipient is a subject who has received a heart transplant, a lung transplant, a liver transplant, or a kidney transplant.

* * * * *